US010021881B2

(12) United States Patent
Jacobson et al.

(10) Patent No.: US 10,021,881 B2
(45) Date of Patent: Jul. 17, 2018

(54) VAPORIZED ADMINISTRATION OF PESTICIDES

(71) Applicant: AGROFRESH INC., Collegeville, PA (US)

(72) Inventors: Richard M. Jacobson, Chalfont, PA (US); Daniel MacLean, Woodland, CA (US); Timothy Malefyt, Stroudsburg, PA (US); Esther Gachango, Davis, CA (US)

(73) Assignee: AGROFRESH INC., Collegeville, PA (US)

( * ) Notice: Subject to any disclaimer, the term of this patent is extended or adjusted under 35 U.S.C. 154(b) by 0 days.

(21) Appl. No.: 15/452,501

(22) Filed: Mar. 7, 2017

(65) Prior Publication Data
US 2017/0251669 A1    Sep. 7, 2017

Related U.S. Application Data

(60) Provisional application No. 62/304,646, filed on Mar. 7, 2016.

(51) Int. Cl.
A01N 43/54    (2006.01)
A01N 25/18    (2006.01)
A01N 25/12    (2006.01)

(52) U.S. Cl.
CPC ............. A01N 43/54 (2013.01); A01N 25/12 (2013.01); A01N 25/18 (2013.01)

(58) Field of Classification Search
CPC ......... A01N 43/54; A01N 25/18; A01N 25/12
See application file for complete search history.

(56) References Cited

U.S. PATENT DOCUMENTS

| | | | |
|---|---|---|---|
| 3,469,933 | A | 9/1969 | Robert |
| 4,843,956 | A | 7/1989 | Lashlee |
| 5,880,188 | A | 3/1999 | Austin et al. |
| 6,305,148 | B1 | 10/2001 | Bowden et al. |
| 7,582,621 | B2 | 9/2009 | Baker et al. |
| 8,669,207 | B1 | 3/2014 | Jacobson et al. |
| 2014/0187570 | A1 | 7/2014 | Sardo |
| 2014/0349853 | A1 | 11/2014 | Maclean et al. |
| 2016/0015034 | A1 | 1/2016 | Bratz et al. |

OTHER PUBLICATIONS

Sholberg et al, Fumigation of Stored Pome Fruit with Hexanal Reduces Blue and Gray Mold Decay, 2007, HortScience, 42(3), pp. 661-616. (Year: 2007).*

Baker, S. J., Y.-K. Zhang, et al. (2006). "Discovery of a New Boron-Containing Antifungal Agent, 5-Fluoro-1,3-dihydro-1-hydroxy-2,1-benzoxaborole (AN2690), for the Potential Treatment of Onychomycosis." Journal of Medicinal Chemistry 49(15): 4447-4450.

Rock, F. L., W. Mao, et al, (2007). "An Antifungal Agent Inhibits an Aminoacyl-tRNA Synthetase by Trapping tRNA in the Editing Site." Science 316(5832): 1759-1761.

(Continued)

Primary Examiner — Trevor Love
(74) Attorney, Agent, or Firm — Barnes & Thornburg LLP

(57) ABSTRACT

The present disclosure relates to methods for administering vaporized pyrimethanil as an antimicrobial to inhibit pathogens of agricultural crops.

16 Claims, 12 Drawing Sheets

(56) References Cited

OTHER PUBLICATIONS

Grinstein et al., "Improved Chemical Control of Botrytis Blight in Roses", Mar. 1997, vol. 25, Supplement 1, pp. 87-92.
Dauthy "Fruit and vegetable processing: Chapter 5.3 Chemical Preservation" FAO Agricultural Services Bulletin, 1995, No. 119.
Reddy et al., "1-MCP, a novel plant growth regulator for regulation of ripening" Agricultural & Horticultural Sciences, Feb. 2014, vol. 2.
"Pubchem CID 91650" Create Date: Jun. 24, 2005; Date Accessed Apr. 24, 2017, p. 3.
International Search Report and Written Opinion, International Application No. PCT/US2017/020935, dated May 24, 2017, 9 pages.

\* cited by examiner

VAPORIZED ADMINISTRATION OF PESTICIDES

CROSS-REFERENCE TO RELATED APPLICATION

This application claims the benefit under 35 USC § 119(e) of U.S. Provisional Patent Application Ser. No. 62/304,646, filed on Mar. 7, 2016, the entire disclosure of which is incorporated herein by reference.

FIELD OF THE PRESENT APPLICATION

The present application relates to methods for administering pyrimethanil as a vapor to inhibit plant pathogens of agricultural crops in a contained environment.

BACKGROUND

Pyrimethanil is a synthetic compound of the chemical group Anilinopyrimidine. Pyrimethanil is known to act as a pesticide, particularly a fungicide, to provide preventative and curative control of diseases of plants, seeds, and crops.

One mechanism of action by which pyrimethanil has been shown to act as a fungicide is to inhibit methionine biosynthesis, and thus affects protein formation and subsequent cell division. Pyrimethanil has also been shown to block the ability of fungi to degrade and digest plants, thereby inhibiting penetration and development of pathogenic disease and infection. Pyrimethanil has also been described as having a thermal decomposition temperature ranging from 189.54° C. to about 344.74° C. (Agriphar Pyrimethanil (ISO) Safety Data Sheet, revised Sep. 7, 2012, version 8.1).

Traditionally, postharvest fungicides are applied to plants, seeds, and crops as a water-based solvent emulsions for use in spray or drench applications during sorting and packing operations. Some crops, such as soft fruits, including berries or table grapes, are very susceptible to fungal pathogens, but are not tolerant of the free moisture present in traditional fungicide applications. Therefore, treatment of soft fruits with traditional fungicides is problematic. Other crops, such as apples and oranges, can tolerate the moisture of traditional fungicides, but the drenching operation typically used to apply a fungicide is costly, time consuming, requires excessive volumes of pesticide treated water, and spreads spores of non-susceptible pathogens that contribute to fungicide-resistant pathogen populations.

Some postharvest fungicide treatments are delivered via fogging, which is typically administered in a cold temperature (below room temperature). However, this technique has problems with uniform distribution onto the crops. For example, deposition rates of a fungicide may be too high, and exceed regulatory maximum residue limits. Alternatively, deposition rates of a fungicide may be too low and fall below the minimum required for efficacy. In addition, fungicide fogging operations are not successfully performed when cooling circulation fans are operating in the room or chamber. These fans are essential to the important fruit cooling preservation process, so having them off during the fungicide fogging operation is a negative feature of this sort of application as it contributes to undesirable warming of the stored crop. In a storage room, fungicide application efficacy is closely tied to uniformity of distribution. Ultimately, more uniformity and even distribution on the crop of pesticide or fungicide treatments improves the efficacy of such treatments to inhibit and/or control plant pathogens.

The present disclosure describes methods of administering traditional pesticides in non-traditional ways for use in antimicrobial protection of crops to inhibit plant pathogens. More specifically, the present disclosure provides methods of using vaporized pyrimethanil as an antimicrobial protection to post-harvest plants, plant parts, and seeds that are advantageous to other previously described antimicrobial treatments of plants. Ultimately, the methods described herein provide beneficial delivery options for established pesticides and application systems.

SUMMARY OF THE INVENTION

The present disclosure provides a method of treating plants or plant parts with an antimicrobial agent. The method comprises heating the antimicrobial compound to form a vapor. The method also comprises cooling the vapor to form a solid. Additionally, the method comprises administering the solid compound to one or more plants or plant parts in a chamber.

The one or more plants or plant parts of the method described herein may comprise a strawberry, a grape, an apple, an orange, or a blueberry. The method may further comprise circulating the solid compound throughout the chamber with fans. Finally, the method further provides that the heating, cooling, or administering steps may be performed using a heating device.

The antimicrobial compound of the present method may be a solid. Further, the solid compound may form microparticles having a size of 2 micron or less. Additionally, the antimicrobial compound of the present disclosure may have a vapor pressure at room temperature that is less than the vapor pressure at room temperature of benzoxaborole.

BRIEF DESCRIPTION OF THE DRAWINGS

A brief description of the drawings is as follows.

DETAILED DESCRIPTION

Figure 1:
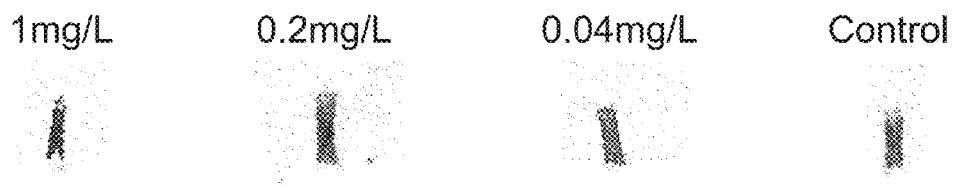
FIG. 1 shows images of *Penicillium digitatum* growth after being inoculated on oranges and treated with vaporized pyrimethanil.

The following numbered embodiments are contemplated and are non-limiting:

1. A method of treating plants or plant parts with an antimicrobial treatment comprising:
   a) preparing the antimicrobial treatment comprising an antimicrobial compound,
   b) volatilizing the antimicrobial compound to form a vapor,
   c) cooling the vapor to form a solid, and
   d) administering the solid antimicrobial compound to one or more plants or plant parts in a chamber.

2. The method of clause 1, wherein the one or more plants or plant parts is selected from the group consisting of a strawberry, a grape, an apple, an orange, and a blueberry.

3. The method of clause 1 or clause 2, wherein the antimicrobial compound is a solid, a gas, a liquid, a vapor, or an aerosol.

4. The method of any one of clauses 1 to 3, wherein the antimicrobial compound is a solid.

5. The method of any one of clauses 1 to 4, wherein the method further comprises circulating the antimicrobial compound throughout the chamber with a source of air.

6. The method of any one of clauses 1 to 5, wherein the antimicrobial compound forms microparticles having a size of 2 micron or less.

7. The method of clause 5 or clause 6, wherein the source of air is a fan.

8. The method of any one of clauses 1 to 7, wherein the volatilizing occurs by sublimation.

9. The method of any one of clauses 1 to 7, wherein the volatilizing occurs by heating.

10. The method of any one of clauses 1 to 8, wherein the sublimation occurs by evaporation.

11. The method of any one of clauses 1 to 10, wherein the antimicrobial compound is in the form of a powder.

12. The method of any one of clauses 1 to 11, wherein the antimicrobial compound is sublimated directly into a vapor.

13. The method of any one of clauses 1 to 12, wherein the antimicrobial compound is a pesticide.

14. The method of any one of clauses 1 to 13, wherein the antimicrobial compound is a fungicide.

15. The method of any one of clauses 1 to 14, wherein the antimicrobial compound is pyrimethanil or an analog or derivative thereof.

16. The method of clause 15, wherein the pyrimethanil or analog or derivative thereof comprises the following structure:

17. The method of any one of clauses 1 to 16, wherein 100% of the antimicrobial compound is volatilized into the vapor.

18. The method of any one of clauses 1 to 17, wherein no thermal degradation of the antimicrobial compound occurs at a temperature ranging from about 300° C. to about 350° C.

19. The method of any one of clauses 1 to 18, wherein the antimicrobial compound is administered at a rate of about 0.001 mg/L to about 5 mg/L.

20. The method of any one of clauses 1 to 19, wherein the antimicrobial treatment further comprises a component selected from the group consisting of a carrier, a preservative gas, a compound, and a chemical.

21. The method of any one of clauses 1 to 20, wherein the preservative gas is $CO_2$.

22. The method of any one of clauses 1 to 20, wherein the preservative gas is $SO_2$.

23. The method of any one of clauses 1 to 21, wherein the $CO_2$ concentration of the antimicrobial treatment ranges from about 4% to about 20%.

24. The method of any one of clauses 1 to 21 and 23, wherein the $CO_2$ concentration of the antimicrobial treatment is about 12%

25. The method of any one of clauses 1 to 20 and 22, wherein the $SO_2$ concentration of the antimicrobial treatment ranges from about 0.01% to about 5%.

26. The method of any one of clauses 1 to 20, wherein the chemical is selected form the group consisting of 1-methylcyclopropene (1-MCP), oxaborole, imazalil, fludioxonil, thiabendazole, and dioadjuvant(s).

27. The method of clause 26, wherein the oxaborole is benzoxaborole.

28. The method of any one of clauses 1 to 27, wherein the antimicrobial compound has a vapor pressure at room temperature that is less than the vapor pressure at room temperature of benzoxaborole.

29. The method of any one of clauses 1 to 28, wherein the method is effective against plant pathogens.

30. The method of any one of clauses 1 to 29, wherein the plant pathogens are fungal pathogens or bacterial pathogens.

31. The method of any one of clauses 1 to 30, wherein the plant pathogens are selected from the group consisting of *Acremonium* spp., *Albugo* spp., *Alternaria* spp., *Ascochyta* spp., *Aspergillus* spp., *Botryodiplodia* spp., *Botryospheria* spp., *Botrytis* spp., *Byssochlamys* spp., *Candida* spp., *Cephalosporium* spp., *Ceratocystis* spp., *Cercospora* spp., *Chalara* spp., *Cladosporium* spp., *Colletotrichum* spp., *Cryptosporiopsis* spp., *Cylindrocarpon* spp., *Debaryomyces* spp., *Diaporthe* spp., *Didymella* spp., *Diplodia* spp., *Dothiorella* spp., *Elsinoe* spp., *Fusarium* spp., *Geotrichum* spp., *Gloeosporium* spp., *Glomerella* spp., *Helminthosporium* spp., *Khuskia* spp., *Lasiodiplodia* spp., *Macrophoma* spp., *Macrophomina* spp., *Microdochium* spp., *Monilinia* spp., *Monilochaethes* spp., *Mucor* spp., *Mycocentrospora* spp., *Mycosphaerella* spp., *Nectria* spp., *Neofabraea* spp., *Nigrospora* spp., *Penicillium* spp., *Peronophythora* spp., *Peronospora* spp., *Pestalotiopsis* spp., *Pezicula* spp., *Phacidiopycnis* spp., *Phoma* spp., *Phomopsis* spp., *Phyllosticta* spp., *Phytophthora* spp., *Polyscytalum* spp., *Pseudocercospora* spp., *Pyricularia* spp., *Pythium* spp., *Rhizoctonia* spp., *Rhizopus* spp., *Sclerotium* spp., *Sclerotinia* spp., *Septoria* spp., *Sphaceloma* spp., *Sphaeropsis* spp., *Stemphyllium* spp., *Stilbella* spp., *Thielaviopsis* spp., *Thyronectria* spp., *Trachysphaera* spp., *Uromyces* spp., *Ustilago* spp., *Venturia* spp., *Verticillium* spp., *Bacillus* spp., *Campylobacter* spp., *Clavibacter* spp., *Clostridium* spp., *Erwinia* spp., *Escherichia* spp., *Lactobacillus* spp., *Leuconostoc* spp., *Listeria* spp., *Pantoea* spp., *Pectobacterium* spp., *Pseudomonas* spp., *Ralstonia* spp., *Salmonella* spp., *Shigella* spp., *Staphylococcus* spp., *Vibrio* spp., *Xanthomonas* spp., and *Yersinia* spp.

32. The method of any one of clauses 1 to 31, wherein the plant pathogens are selected from the group consisting of *Botrytis cinerea, Mucor piriformis, Fusarium sambucinum, Aspergillus brasiliensis*, and *Peniciliium expansum*.

33. The method of any one of clauses 1 to 32, wherein the chamber is sealed.

34. The method of any one of clauses 1 to 33, wherein the chamber is air-tight.

35. The method of any one of clauses 1 to 34, wherein the temperature of the chamber ranges from about −2° C. to about 25° C.

36. The method of any one of clauses 1 to 35, wherein the temperature of the chamber ranges from about 0° C. to about 23° C.

37. The method of any one of clauses 1 to 36, wherein the chamber is semipermeable or impermeable.

38. The method any one of clauses 1 to 37, wherein the chamber is made of a material selected from the group consisting of plastic, glass, wood, and metal.

39. The method any one of clauses 1 to 38, wherein the chamber comprises a port, an outlet, or both.

40. The method of any one of clauses 1 to 39, wherein the one or more plants or plant parts are manually or robotically placed in the chamber.

41. The method of any one of clauses 1 to 40, wherein the chamber is selected from the group consisting of a cold-storage room, a marine container, an air container, a traincar, a local vehicle, a transport truck, a trailer, a box, a pallet-wrap, a greenhouse, a grain silo, a gymnasium, a barn, and an industrial storage facility.

42. The method any one of clauses 1 to 41, wherein the time to administer the antimicrobial treatment ranges from about 1 hour to about 5 days.

43. The method of any one of clauses 1 to 42, wherein the method is performed using a heating device.

44. A heating device adapted to perform the method of any one of clauses 1 to 43, wherein the heating device comprises:
 a heating element,
 a heating chamber,
 a power source,
 the antimicrobial compound,
 and one or more orifices.

45. The heating device of clause 44, wherein the heating chamber comprises a copper tube.

46. The heating device of clause 44, wherein the heating chamber comprises a glass tube.

47. The heating device of clause 44, wherein the heating chamber comprises a source of air.

48. The heating device of clause 47, wherein the source of air is a fan.

49. The heating device of any one of clauses 44 to 48, wherein the power source is internal or external to the heating device.

50. The heating device of any one of clauses 44 to 49, wherein the power provided by the power source is selected from the group consisting of electrical power, gas power, and wind power.

51. The heating device of any one of clauses 44 to 50, wherein the temperature of the heating chamber ranges from about 90° C. to about 300° C.

52. The heating device of any one of clauses 44 to 50, wherein the temperature of the heating chamber does not fall below 100° C.

53. The heating device of any one of clauses 44 to 50, wherein the temperature of the heating chamber does not fall below about 96° C. to about 98° C.

54. The heating device of any one of clauses 44 to 53, wherein the one or more orifices are located at the proximal end of the heating device.

55. The heating device of any one of clauses 44 to 54, wherein the stability of the antimicrobial compound is maintained at temperatures ranging from about 300° C. to about 350° C.

56. A method of using the heating device of any one of clauses 44 to 55, the method comprising:
 a) loading the antimicrobial treatment comprising the antimicrobial compound onto the heating chamber,
 b) turning on the power source to heat up the heating element and the heating chamber,
 c) volatilizing the antimicrobial compound into a vapor, and
 d) releasing the vapor from the one or more orifices of the heating device into the chamber.

57. The method of clause 56, wherein the antimicrobial compound is placed directly onto the surface of the heating chamber.

58. The method of clause 56, wherein the antimicrobial compound is placed directly into the heating chamber.

59. The method of clause 58, wherein the antimicrobial compound is placed into the glass tube comprised within the heating chamber.

60. The method of clause 56, wherein the antimicrobial compound is dissolved within a solvent.

61. The method of clause 60, wherein the solvent is a volatile solvent.

62. The method of clause 60 or clause 61, wherein the solvent comprising the dissolved antimicrobial compound is placed onto a compound carrier.

63. The method of clause 62, wherein the compound carrier is solid.

64. The method of clauses 62 or clause 63, wherein the compound carrier is an absorbent material.

65. The method of any one of clauses 62 to 64, wherein the compound carrier is cotton.

66. The method of any one of clauses 62 to 64, wherein the compound carrier is non-flammable.

67. The method of any one of clauses 62 to 66, wherein the solvent is dried from the compound carrier to form a dry compound carrier.

68. The method of clause 67, wherein the solvent is evaporated from the compound carrier to form the dry compound carrier.

69. The method of any one of clauses 56 to 68, wherein the heating device penetrates the chamber.

70. The method of any one of clauses 56 to 69, wherein the heating device is sealed within the chamber.

71. The method of any one of clauses 56 to 70, wherein the chamber is air-tight.

72. The method of any one of clauses 56 to 71, wherein the vapor solidifies upon release from the heating device.

73. The method of any one of clauses 56 to 72, wherein the vapor forms microparticles.

74. The method of clause 73, wherein the microparticles are solid.

75. The method of clause 73 or clause 74, wherein the microparticles are powder.

76. The method of any one of clauses 73 to 75, wherein the size of the microparticles is 2 microns or less.

77. The method of any one of clauses 73 to 76, wherein the size of the microparticles is less than 1 micron.

78. The method of any one of clauses 73 to 77, wherein the microparticles are distributed throughout the chamber by a source of air flow.

79. The method of clause 78, wherein the source of air flow is comprised in the heating device, the chamber, or both.

80. The method of clause 78 or clause 79, wherein the source of air flow is a fan.

81. The method of any one of clauses 73 to 80, wherein the microparticles enable uniform distribution of the antimicrobial compound without wetting.

The term "plant(s)" and "plant parts" include, but not limited to, whole plants, plant cells, and plant tissues, such as leaves, calli, stems, pods, roots, fruits, flowers or flower parts, pollen, seeds, egg cells, zygotes, cuttings, cell or tissue cultures, or any other part or product of a plant. A class of plants that may be used in the present invention is generally as broad as the class of higher and lower plants including, but not limited to, dicotyledonous plants, monocotyledonous plants, agronomic crops, and horticultural crops, which include, but are not limited to, vegetable crops, fruit crops, edible nuts, flowers and ornamental crops, nursery crops, aromatic crops, and medicinal crops.

More specifically, horticultural crops of the present disclosure include, but are not limited to, fruit selected from, but not limited to, almond, apple, avocado, banana, berries (including strawberry, blueberry, raspberry, blackberry, currents and other types of berries), carambola, cherry, citrus (including orange, lemon, lime, mandarin, grapefruit, and other citrus), coconut, fig, grape, guava, kiwifruit, mango, nectarine, melons (including cantaloupe, muskmelon, watermelon, and other melons), olive, papaya, passionfruit, peach, pear, persimmon, pineapple, plum, and pomegranate.

A vegetable is selected from the group, which includes, but is not limited to, asparagus, beet (including sugar and fodder beet), bean, broccoli, cabbage, carrot, cassava, cauliflower, celery, cucumber, eggplant, garlic, gherkin, leafy greens (lettuce, kale, spinach, and other leafy greens), leek, lentil, mushroom, onion, peas, pepper (sweet, bell or hot), potato, pumpkin, sweet potato, snap bean, squash, tomato and turnip. Nursery plant or flower or flower part is selected from the group, which include, but not limited to, rose, carnation, geranium, gerbera, lily, orchid, or other cut-flowers or ornamental flowers, flower bulbs, shrub, deciduous or coniferous tree.

Crops of the present disclosure may also include, but are not limited to, cereal and grain crops (e.g., corn, rice, and wheat), grain legume or pulses (e.g., beans and lentils), oilseed crops (e.g., soybean, sunflower, and canola), feed for industrial use, pasture and forage crops, fiber crops (e.g., cotton, flax, and hemp), sugar crops (e.g., sugar beets and sugarcane), and starchy root and tuber crops (e.g., beets, carrots, potatoes, and sweet potatoes).

The terms "microorganism" or "plant pathogen" refers to organisms, such as *Botrytis cinerea*, *Mucor piriformis*, *Fusarium sambucinum*, *Aspergillus brasiliensis*, and *Peniciliium expansum*. Additional pathogens encompassed by the present invention include, but are not limited to *Acremonium* spp., *Albugo* spp., *Alternaria* spp., *Ascochyta* spp., *Aspergillus* spp., *Botryodiplodia* spp., *Botryospheria* spp., *Botrytis* spp., *Byssochlamys* spp., *Candida* spp., *Cephalosporium* spp., *Ceratocystis* spp., *Cercospora* spp., *Chalara* spp., *Cladosporium* spp., *Colletotrichum* spp., *Cryptosporiopsis* spp., *Cylindrocarpon* spp., *Debaryomyces* spp., *Diaporthe* spp., *Didymella* spp., *Diplodia* spp., *Dothiorella* spp., *Elsinoe* spp., *Fusarium* spp., *Geotrichum* spp., *Gloeosporium* spp., *Glomerella* spp., *Helminthosporium* spp., *Khuskia* spp., *Lasiodiplodia* spp., *Macrophoma* spp., *Macrophomina* spp., *Microdochium* spp., *Monilinia* spp., *Monilochaethes* spp., *Mucor* spp., *Mycocentrospora* spp., *Mycosphaerella* spp., *Nectria* spp., *Neofabraea* spp., *Nigrospora* spp., *Penicillium* spp., *Peronophythora* spp., *Peronospora* spp., *Pestalotiopsis* spp., *Pezicula* spp., *Phacidiopycnis* spp., *Phoma* spp., *Phomopsis* spp., *Phyllosticta* spp., *Phytophthora* spp., *Polyscytalum* spp., *Pseudocercospora* spp., *Pyricularia* spp., *Pythium* spp., *Rhizoctonia* spp., *Rhizopus* spp., *Sclerotium* spp., *Sclerotinia* spp., *Septoria* spp., *Sphaceloma* spp., *Sphaeropsis* spp., *Stemphyllium* spp., *Stilbella* spp., *Thielaviopsis* spp., *Thyronectria* spp., *Trachysphaera* spp., *Uromyces* spp., *Ustilago* spp., *Venturia* spp., and *Verticillium* spp., and bacterial pathogens, such as *Bacillus* spp., *Campylobacter* spp., *Clavibacter* spp., *Clostridium* spp., *Erwinia* spp., *Escherichia* spp., *Lactobacillus* spp., *Leuconostoc* spp., *Listeria* spp., *Pantoea* spp., *Pectobacterium* spp., *Pseudomonas* spp., *Ralstonia* spp., *Salmonella* spp., *Shigella* spp., *Staphylococcus* spp., *Vibrio* spp., *Xanthomonas* spp., and *Yersinia* spp.

The terms "vaporized," "volatilized," and "aerosolized" refer to the physical transformation of an element, object, or compound that is exposed to intense heat. Often, a vapor or gas will result when the element, object, or compound in liquid phase or solid phase is exposed to intense heat.

Vaporization may include the phase transition of an element or compound from the liquid phase to a vapor. Vaporization may occur by evaporation when the partial pressure of the vapor is less than the equilibrium vapor pressure, where the phase transition from liquid to vapor occurs below the boiling point of the said compound at a given pressure. Vaporization of a liquid to gas may also occur at or above the boiling point. Boiling occurs when the equilibrium vapor pressure of the substance is greater than or equal to the environmental pressure.

Vaporization may also include the phase transition of an element or compound from the solid phase to a vapor. For example, the terms "sublimated" or "sublimation" refer to the phase transition of an element or compound from the solid phase to a vapor. Often, sublimation is the direct phase transition from the solid phase to the gas phase, skipping the intermediate liquid phase. Alternatively, "sublimation" may also include "evaporation" of a solid compound, when the solid compound is first exposed to its melting temperature, and caused to melt into a liquid or pseudo-liquid form (e.g., softening, gel, paste, etc.) before its final transition into a vapor or gaseous phase.

Compounds and Components of the Present Methods

The methods of the present disclosure are directed to using pyrimethanil compounds as an antimicrobial to treat plants or plant parts. The methods of the present disclosure to treat plant or plant parts comprise, consist essentially of, or consist of pyrimethanil compounds. One exemplary embodiment of a pyrimethanil compound (4,6-Dimethyl-N-phenylpyrimidin-2-amine or 4, 6-Dimethyl-N-phenyl-2-pyrimidinamine) of the present method is:

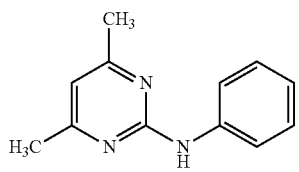

or an analog or derivative thereof.

Pyrimethanil is an active ingredient that may be used individually or as a mixture or combination with other compounds or a carrier. For example, the pyrimethanil compound may also be used in combination with preservative gases or chemicals to form a pyrimethanil co-treatment. The pyrimethanil compound may also be used in combination with a carrier to form a pyrimethanil treatment. The pyrimethanil treatment provides antimicrobial protection to plants or plant parts when administered, applied, or exposed to plants or plant parts.

The melting temperature for pyrimethanil ranges from about 96° C. to about 98° C. At or above about 120° C., pyrimethanil compounds experience mass loss at a steady state, which is gradual due to evaporation. Since the observed loss of pyrimethanil occurs above its melting temperature, the loss of active ingredient is considered to include evaporation, rather than direct sublimation, since the loss of active ingredient occurs from the melted form. Moreover, no molecular changes to the pyrimethanil active compound is observed to occur during the sublimation process.

Pyrimethanil may be used in any form, including, but not limited to, a solid (e.g., a powder), a gas, a vapor, or an aerosol composition. In particular, pyrimethanil may be used in the form of a gas, and/or a vapor, ("vapor") when sufficient heat is applied to the solid pyrimethanil. In one embodiment, a pyrimethanil compound or a plurality of pyrimethanil compounds may be vaporized using heat to convert a solid to a liquid composition of pyrimethanil and then into a vapor. In another embodiment, a pyrimethanil compound or a plurality of pyrimethanil compounds may be vaporized using heat to convert a solid composition of pyrimethanil into a vapor by sublimation. In an illustrative embodiment, a powder composition of pyrimethanil is heated in order to convert the solid composition directly into a vapor by sublimation.

Typically, at room temperature and lower, pyrimethanil exists as a solid. However, when the temperature increases, such as in response to heat, the solid pyrimethanil volatilizes or vaporizes to become a gas, a vapor, or an aerosol ("vapor"). Heat may be applied to the pyrimethanil compound by any method that will cause the pyrimethanil to vaporize. However, in one embodiment of the present method, heat may be applied to the pyrimethanil compound using an apparatus or device. In an illustrative embodiment of the present method, a heating device or apparatus is used to vaporize technical pyrimethanil (see Example 7).

For example, a heating device of the present disclosure comprises a heating element surrounding a heating chamber or a container (e.g., a copper tube). The heating element is capable of producing high temperatures needed to achieve the vaporization temperature of a technical solid active ingredient, such as pyrimethanil.

The active ingredient is placed into the heating chamber in a number of possible ways. For example, the solid active ingredient (e.g., powder) may be placed directly on the surface of the heating chamber or heating element, or placed into a glass tube that is inserted into the heating chamber of the device. Alternatively, the solid active ingredient may be dissolved with a volatile solvent, and the desired amount of dissolved active may be placed in or on a solid carrier, such as cotton or a non-flammable absorbent material. If a solvent is used, the solvent may be evaporated, and the dry carrier material containing active ingredient is loaded into the heating chamber. Any other ways to load the desired amount of active technical ingredient into the heating chamber of the heating device are also encompassed by the present disclosure.

The heating device also comprises a power source. The power source may be internal or external to the heating device and provides power to the heating element by any means, including electrical, gas, or wind power. When the power is turned on, heat is applied to the heating chamber containing the active ingredient, which vaporizes into a gaseous state ("vapor").

Typically, the temperature of the heating chamber may range from about 90° C. to about 300° C. For example, the heating chamber may range from about 100° C. to about 300° C. and from about 100° C. to about 200° C., such that lower temperatures in the heating chamber induce slower vaporization of the active, while higher temperatures induce faster vaporization of the active.

While total loss and/or degradation of pyrimethanil active ingredient may occur between about 200° C. to about 300° C., in some embodiments of the pyrimethanil composition of the instant disclosure, no thermal degradation of pyrimethanil was observed at temperatures at or about 300° C. to about 350° C. These results are unexpectedly surprising and contrary to the known thermal decomposition range of 189.54-344.74° C. for pyrimethanil.

A source of low volume air flow is also comprised by the heating device. For example, a fan or some mechanism to push air through the heating chamber of the device is necessary. The air flow source (e.g., a fan) will push air through the heating chamber comprising the vaporized active ingredient and through the proximal end portion of the heating device through one or more orifices or openings located at the proximal end of the heating device. The air flow through the heating device should be capable of being maintained and should be maintained at a speed or velocity that is low enough and/or slow enough to prevent the air traveling through the device from cooling the heating chamber (comprising the active ingredient) below the temperature upon which the vaporized active ingredient is formed. For example, when vaporizing pyrimethanil, typically the temperature of the heating chamber should not fall lower than 100° C., and further not below 96° C.-98° C., the melting temperature of the pyrimethanil.

The source of air flow in the heating device may push air and active ingredient out of the orifice(s) of the device and directly into a closed environment, container, or chamber. The heating device may penetrate the chamber and may be sealed therein, such that a significant amount of vaporized active ingredient is not lost to the environment. The chamber may comprise plants or plant parts, such as fruits, flowers, or vegetables, to be treated with the vaporized active ingredient in order to control plant pathogens.

The chamber is typically held at a temperature suitable for storing fruits, flowers, or vegetables. For example, the temperature of the chamber may range from about −2° C. to about 25° C., and often ranges from about 0° C. to about 23° C., which is significantly cooler than the temperature of the heating chamber of the device. When the active vapor moves from the warmer temperature of the heating device into the cooler temperature of the chamber, the vaporized active ingredient immediately resolidifies. The cooled vapor forms tiny solid microparticles of active pyrimethanil powder that individually resolidified in their submicron state. The solid active microparticles are distributed and dispersed throughout the chamber by the source of air flow of the heating device in addition to other sources of air flow and movement that may be present in the chamber (e.g., fans). For example, vaporized pyrimethanil immediately transitions back into its solid form (e.g., powder) upon its entrance into the chamber.

The size of the solid pyrimethanil microparticles after vaporization may be from about less than 1 micron (submicron size), from about 1 micron or less, or from less than 1 micron to about 5 microns, from about 0.5 microns to about 5 microns, from about 0.5 microns to about 2 microns, from about 1 micron to about 1.5 microns, about 1 micron to about 2 microns, about 0.5 microns to about 1.5 microns, about 1.5 microns to about 2 microns, about 1 micron to about 5 microns, and about 2 microns to about 5 microns. Other application techniques, such as fogging and drenching, use particle sizes ranging from about 2 microns to about 90 microns. The extremely small to submicron size of the solid pyrimethanil microparticles that form after vaporization in the present method, enables uniform and even distribution and dispersion of the active ingredient for improved efficacy of fungicide or pesticide treatments of plants and plant parts over prior art methods.

In particular, the small solid microparticles are much more easily circulated and distributed in a chamber with fans, while fans cannot be used in some prior art methods (e.g., fogging). Moreover, the small solid particles enable uniform distribution of the active ingredient on the plants or plant parts without wetting, such as with water or a solvent. Thus, the present method provides a unique way of treating plants and plant parts without wetting the fruit, but still enabling uniform application and efficacious disease control and inhibition of plant pathogens.

The active pyrimethanil compounds may be applied to plants or plant parts in any volume of a contained environment or chamber and may be used on plants or plant parts in greenhouse production, and post-harvest during field packing, palletization, in-box, during storage, and throughout the distribution network. A contained environment or chamber of the present disclosure may be any contained volume of headspace from which a gas, vapor, or chemical cannot readily escape once it has been introduced. For example, a contained environment or chamber may be made of plastic, glass, wood, metal or any other typical semipermeable or impermeable construction materials used to store or transport plants or plant parts.

Any contained space that is used to hold plants or crops may be used as a chamber in the present method. The chamber of the present disclosure comprises a headspace (i.e., volume of capacity) that may be of any size that is large enough to hold plants and plant parts to be treated. For example, a contained space or chamber includes, but is not limited to, a cold-storage room, a marine container, an air container, a traincar or local vehicle, a transport truck or trailer, a box or a pallet-wrap, a greenhouse, a grain silo or similar. Further, gymnasiums, barns, and other large industrial storage facilities are within the scope of the present disclosure of a chamber. In addition, minimally-processed packaged products (e.g., packaged vegetables or fruits) may also be treated with the method described herein.

The chamber may have a port (e.g., a bulkhead septum port) for the introduction or release of the chemical treatment as a vapor or aerosol. The contained environment chamber may also have an outlet to vent or release the unused portion of the treatment carrier or to maintain atmospheric pressure.

One advantage of the method of the present disclosure over the prior art is that a carrier is not required to activate or deliver the pyrimethanil compound to plants or plant parts. In other words, the method of the present invention may be used with about 100% active ingredient, such as pyrimethanil. Since the present method is able to only use active solid ingredient to treat plants and plant parts Vaporized pyrimethanil treatments may be applied to the plants or plants parts at a rate that is reported as the amount (milligrams, mg) of active ingredient (i.e., pyrimethanil compound) per volume (liter, L) of chamber headspace. For example, the rate that the pyrimethanil treatment may be effectively applied in a chamber and/or to plants may range from 0.001 mg/L to 5 mg/L. For example, the rate of the pyrimethanil treatment may be from about 0.01 mg/L to about 3 mg/L, from about 0.01 mg/L to about 4 mg/L, from about 0.01 mg/L to about 0.2 mg/L, from about 0.01 mg/L to about 1 mg/L, from about 1 mg/L to about 5 mg/L from about 0.5 mg/L to about 3 mg/L, from about 0.01 mg/L to about 0.05 mg/L, from about 0.01 mg/L to about 0.04 mg/L, from about 0.01 mg/L to about 0.03 mg/L, from about 0.1 mg/L to about 0.5 mg/L, from about 0.1 mg/L to about 0.4 mg/L, from about 0.1 mg/L to about 0.3 mg/L, from about 0.1 mg/L to about 0.2 mg/L, from about 0.001 mg/L to about 0.2 mg/L, from about 0.001 mg/L to about 0.05 mg/L, from about 0.001 mg/L to about 0.04 mg/L, from about 0.001 mg/L to about 3 mg/L, and at about 0.01 mg/L, about 0.03 mg/L, about 0.04 mg/L, about 0.1 mg/L, about 0.2 mg/L, about 0.3 mg/L, and about 1 mg/L.

Additional preservative gases of the method described herein may be included in the treatment chamber, but are not limited to, carbon dioxide ($CO_2$) and sulfur dioxide ($SO_2$). While any concentration of preservative gas or chemical that provides the antimicrobial effect described herein may be utilized, a percent of $CO_2$ gas that may be used in the present method includes, but is not limited to, from about 4% to about 20%, from about 5% to about 18%, from about 6% to about 17%, from about 7% to about 15%, from about 8% to about 14%, from about 8% to about 13%, from about 8% to about 12%, from about 5% to about 14%, from about 6% to about 13%, from about 7% to about 13%, and at about 8%, about 9%, about 10%, about 11%, about 12%, about 13%, and about 14%. A percent of $SO_2$ gas that may be used in the present method includes, but is not limited to, from about 0.01% to about 5%, from about 0.02% to about 4%, from about 0.03% to about 3%, from about 0.04% to about 2%, from about 0.05% to about 1%, and from about 0.01% to about 1%.

Additional chemicals that may be combined with pyrimethanil compound in the present disclosure include, but are not limited to, 1-methylcyclopropene (1-MCP), oxaboroles (e.g., benzoxaborole), imazalil, fludioxonil, thiabendazole, dioadjuvant(s), and other commercial pesticides. Further chemicals that may be used in the present method include some that have been federally recognized. For example, Food, Drug and Cosmetic Act §§ 201 and 409 Generally Recognized As Safe (GRAS) compounds and Federal Insecticide, Fungicide, and Rodenticide Act (FIFRA) § 25(b) chemicals, including eugenol, clove, thyme or mint oils), natural compounds, or compounds derived from natural sources may also be used in the present method.

It should be noted that use of additional volatile compounds alone or in combination with pyrimethanil in the present method may require additional or less heat to vaporize the active ingredients. It has been determined that generally the higher the vapor pressure and/or the smaller the molecules of the active ingredient, the less heat will be required to vaporize that active ingredient. For example, solid benzoxaborole fungicide has a relatively high vapor pressure at room temperature (i.e., about 0.036 Torr at 25° C.) and is inherently volatile, so benzoxaborole would require the addition of much less heat to vaporize in the present method as compared to pyrimethanil. On the other hand, pyrimethanil has a relatively low vapor pressure at room temperature (i.e., about $2.2 \times 10^{-3}$ Pa at 25° C.). Pyrimethanil requires the addition of much more heat to sublimate or vaporize at room temperature than does benzoxaborole. Thus, heat must be adjusted accordingly to properly vaporize co-treatments of active ingredients used in the method of the present disclosure, such as, for example, pyrimethanil and 1-methylcyclopropene or pyrimethanil and benzoxaborole.

Thus, the present method encompasses an active antimicrobial compound that has a vapor pressure at room temperature that is less than the vapor pressure at room temperature of benzoxaborole. Moreover, the present disclosure includes the use of such a low vapor pressure compound, such as pyrimethanil, alone or in combination with other active compounds as described herein.

Any plants or plant parts (e.g., flowers), plant cells, or plant tissues may be treated using the present method. A class of plants that may be treated in the present invention is generally as broad as horticultural crops. Horticultural crops, include, but are not limited to, vegetable crops, fruit crops, edible nuts, flowers and ornamental crops, nursery crops, aromatic crops, and medicinal crops. More specifically, fruits (e.g., grapes, apples, oranges, pears, persimmons, and bananas) and berries (e.g., strawberries, blackberries, blueberries, and raspberries) are plants encompassed by the present disclosure. It should be noted that any species of berries or fruits may be used in the present invention (e.g., Table grapes).

Methods of Using Pyrimethanil Compounds

The present disclosure is directed to methods of providing antimicrobial protection to plants and plant parts from plant pathogens. More specifically, fungal plant pathogens may be treated, prevented, or eradicated by the method described herein. Exemplary, pathogens encompassed by the present disclosure include, but are not limited to, *Botrytis cinerea, Mucor piriformis, Fusarium sambucinum, Aspergillus brasiliensis*, and *Peniciliium expansum*. Additional pathogens encompassed by the present invention include, but are not limited to *Acremonium* spp., *Albugo* spp., *Alternaria* spp., *Ascochyta* spp., *Aspergillus* spp., *Botryodiplodia* spp., *Botryospheria* spp., *Botrytis* spp., *Byssochlamys* spp., *Candida* spp., *Cephalosporium* spp., *Ceratocystis* spp., *Cercospora* spp., *Chalara* spp., *Cladosporium* spp., *Colletotrichum* spp., *Cryptosporiopsis* spp., *Cylindrocarpon* spp., *Debaryomyces* spp., *Diaporthe* spp., *Didymella* spp., *Diplodia* spp., *Dothiorella* spp., *Elsinoe* spp., *Fusarium* spp., *Geotrichum* spp., *Gloeosporium* spp., *Glomerella* spp., *Helminthosporium* spp., *Khuskia* spp., *Lasiodiplodia* spp., *Macrophoma* spp., *Macrophomina* spp., *Microdochium* spp., *Monilinia* spp., *Monilochaethes* spp., *Mucor* spp., *Mycocentrospora* spp., *Mycosphaerella* spp., *Nectria* spp., *Neofabraea* spp., *Nigrospora* spp., *Penicillium* spp., *Peronophythora* spp., *Peronospora* spp., *Pestalotiopsis* spp., *Pezicula* spp., *Phacidiopycnis* spp., *Phoma* spp., *Phomopsis* spp., *Phyllosticta* spp., *Phytophthora* spp., *Polyscytalum* spp., *Pseudocercospora* spp., *Pyricularia* spp., *Pythium* spp., *Rhizoctonia* spp., *Rhizopus* spp., *Sclerotium* spp., *Sclerotinia* spp., *Septoria* spp., *Sphaceloma* spp., *Sphaeropsis* spp., *Stemphyllium* spp., *Stilbella* spp., *Thielaviopsis* spp., *Thyronectria* spp., *Trachysphaera* spp., *Uromyces* spp., *Ustilago* spp., *Venturia* spp., and *Verticillium* spp., and bacterial pathogens, such as *Bacillus* spp., *Campylobacter* spp., *Clavibacter* spp., *Clostridium* spp., *Erwinia* spp., *Escherichia* spp., *Lactobacillus* spp., *Leuconostoc* spp., *Listeria* spp., *Pantoea* spp., *Pectobacterium* spp., *Pseudomonas* spp., *Ralstonia* spp., *Salmonella* spp., *Shigella* spp., *Staphylococcus* spp., *Vibrio* spp., *Xanthomonas* spp., and *Yersinia* spp.

Pyrimethanil treatments may be applied to the plants or plant parts inside of a container or chamber. Typically, the plants or plant parts are manually or robotically placed in the chamber, and the chamber is then sealed. The pyrimethanil treatment may then be applied to the sealed chamber comprising the plants or plant parts via the port (e.g., a bulkhead septum port) or by a device inside the room or container.

The pyrimethanil treatment is applied to the sealed chamber for an initial time period. For example, the plants may be exposed to the pyrimethanil treatment in the sealed container for the initial time period ranging from about 1 hour to about 5 days (120 hours), from about 1 day to about 4 days, from about 2 days to about 3.5 days, from about 2 days to about 3.5 days, and for about 3 days. The temperature of the chamber may be in a range from about −2° C. to about 25° C., and often from about 0° C. to about 23° C.

After the initial time period in which the treatment is exposed to the plants or plant parts in the sealed chamber, the chamber may be left sealed or unsealed. The plants or plant parts can then remain in the contained environment chamber or stored in another storage facility of controlled atmosphere or regular atmosphere until ready for shipment, sale or consumption. The temperature of the chamber or storage facility typically ranges from about −2° C. to about 25° C., and often from about 0° C. to about 23° C.

After expiration of the secondary time period, inhibition of plant pathogens may be assessed. For example, in vitro samples may have the growth of the pathogen on agar or in media assessed, evaluated, and compared to a control sample where no pyrimethanil treatment was administered or different treatment conditions were applied. Similarly, in vivo samples may have the severity and incidence of fungal, bacterial, or pathogenic disease assessed, evaluated, and compared to a control sample where no pyrimethanil treatment was administered or different treatment conditions were applied.

EXAMPLES

Illustrative embodiments of the methods of the present disclosure are provided herein by way of examples. While the concepts and technology of the present disclosure are susceptible to broad application, various modifications, and alternative forms, specific embodiments will be described here in detail. It should be understood, however, that there is no intent to limit the concepts of the present disclosure to the particular forms disclosed, but on the contrary, the intention is to cover all modifications, equivalents, and alternatives consistent with the present disclosure and the appended claims. The following experiments were used to determine the effect of different concentrations of vaporized pyrimethanil compound administered to plants or plant parts or in order to provide antimicrobial protection to the plants or plant parts from plant pathogens.

Example 1: Vaporized Pyrimethanil Treatment on Pathogens (In Vitro)

An in vitro assay was used to evaluate the ability of pyrimethanil to vaporize in order to control the infection of various pathogenic microorganisms when applied to the plants and plant parts. For in vitro experiments, a 12-well microtiter plate, 6-well, or a 10-cm Petri plates each containing 7.5 ml, 16.5 or 22 ml volumes, respectively, of half strength Potato Dextrose Agar (PDA) were prepared. Each well or plate was inoculated with 1 microliter (µL) of $1 \times 10^5$ spores/ml of the appropriate pathogenic spore suspension (e.g., Botrytis cinerea, Penicillium expansum, Glomerella cingulata, Penicillium digitatum, Aspergillus flavus, Colletotrichum acutatum, Fusarium sambucinum, and Geotrichum candidum) by spotting the pathogen on the center of the agar well or plate. The inoculated microtiter or Petri plate was then sealed with a breathable film. One set of triplicate plates for each pathogen was placed inside the bottom of an air-tight 36-L desiccator chamber and closed with secure clamps.

An appropriate amount of pyrimethanil to achieve a final headspace concentration of 1 mg/L, 0.3 mg/L, and 0.1 mg/L was dissolved in acetone and 100 µL of the solution was pipetted into a small glass tube. The tube was then placed inside a pre-heated vaporization device (0.5" OD by 6" long thermostatically heated copper tube mounted to a 0.5 L/min low flow fan) set at 60° C. for 1 minute to allow the acetone to evaporate. Evaporation of the acetone left behind solid crystals of pyrimethanil.

Pyrimethanil was then introduced into the cabinets of the chamber containing the agar plates by using the vaporization device set at 180° C. The tube of the device was attached to a port on the side of the chamber that allowed airflow of the pyrimethanil vapor into the chamber. The chamber was at room temperature during administration of the pyrimethanil. The chambers were then incubated for three (3) days at 23° C. After incubation, post-treatment growth inhibition of each in vitro pathogen was measured on the inoculated plates and compared to control samples.

The outcome of this in vitro experiment is summarized in Table 1. Results demonstrate that the present method comprising vaporized pyrimethanil provides good in vitro inhibition of antimicrobial growth of multiple pathogens inoculated on agar plates. In particular, all three concentrations of pyrimethanil (i.e., 1 mg/L, 0.3 mg/L, and 0.1 mg/L) were able to completely inhibit growth of A. flavus and P. digitatum. Both the 1 mg/L and 0.3 mg/L concentrations of pyrimethanil were also able to totally inhibit growth of P. expansum, while the 0.1 mg/L concentration of pyrimethanil inhibited 92.4% of P. expansum growth. Pyrimethanil concentrations of 1 mg/L, 0.3 mg/L, and 0.1 mg/L were also able to inhibit growth of B. cinerea by 95.2%, 92.1%, and 91.9%, respectively. Similarly, pyrimethanil concentrations of 1 mg/L, 0.3 mg/L, and 0.1 mg/L were also able to inhibit growth of C. acutatum by 89.7%, 90.0%, and 100%, respectively. However, all concentrations of pyrimethanil were effective in controlling G. candidum and G. cingulata, both of which were inhibited by 75.2% and 77.3%, respectively, at the maximum 1 mg/L concentration. Ultimately, Table 1 demonstrates that the present method using vaporized pyrimethanil may be used to inhibit growth of plant pathogens inoculated on agar plates.

TABLE 1

In vitro assay of vaporized pyrimethanil to inhibit pathogenic fungal growth.

| Pathogens | Mycelial Growth Inhibition (%) | | |
|---|---|---|---|
|  | 1 mg/L | 0.3 mg/L | 0.1 mg/L |
| A. flavus | 100.0 | 100.0 | 100.0 |
| P. digitatum | 100.0 | 100.0 | 100.0 |
| P. expansum | 100.0 | 100.0 | 92.4 |
| B. cinerea | 95.2 | 92.1 | 91.9 |
| F. sambucinum | 92.2 | 89.4 | 58.3 |
| C. acutatum | 89.7 | 90.0 | 100.0 |
| G. candidum | 75.2 | 73.1 | 57.8 |
| G. cingulata | 77.3 | 62.1 | 31.5 |

Example 2: Vaporized Pyrimethanil Treatment on P. Digitatum (In Vivo)

An in vivo assay was used to evaluate the ability of vaporized pyrimethanil to to control pathogenic infection of oranges by Penicillium digitatum. Two oranges (per repetition, in triplicate) were placed in a clamshell, and three fresh wounds were made near the equatorial region of each fruit. Each wound was then inoculated with 30 µL of $1 \times 10^6$ spores/mL suspension of P. digitatum. Clamshells were then placed at the bottom of a 36-L acrylic desiccator chamber in triplicate.

An appropriate amount of pyrimethanil to achieve a final treatment concentration of 1 mg/L, 0.2 mg/L, or 0.04 mg/L was dissolved in acetone and 100 µL of the solution was pipetted into a small glass tube. This tube was then placed inside a preheated vaporization device (0.5" OD by 6" long thermostatically heated copper tube mounted to a 0.5 L/min low flow fan) set at 60° C. for 1 minute to allow the acetone to evaporate, leaving behind the solid crystals of pyrimethanil.

Pyrimethanil was then introduced into the contained headspace through the bulkhead port by using the vaporization device as described in Example 1 set at 180° C. The chambers were then incubated at 21° C. for three (3) days. After incubation, fruits were evaluated daily for an additional 2 days at 21° C. Fruits were evaluated in order to observe growth of water-soaked lesions and fungal sporulation diameter (both measured in millimeters, mm).

The outcome of this in vivo experiment is summarized in Table 2 and FIG. 1. Results demonstrate that the present method comprising vaporized pyrimethanil provides good in vivo inhibition of *P. digitatum* antimicrobial growth inoculated in oranges. More specifically, these data indicate that vaporized pyrimethanil provides inhibition of growth of *P. digitatum* water-soaked lesions and fungal sporulation in oranges.

In particular, on Day 2, control oranges showed water-soaked lesions and fungal sporulation reaching 38.2 mm and 22.4 mm, respectively. However, all three concentrations of pyrimethanil (i.e., 1 mg/L, 0.2 mg/L, and 0.04 mg/L) were able to completely inhibit growth of water soaked lesions on oranges by Day 2, except for 1.5 mm of lesions observed on oranges treated with the 0.2 mg/L pyrimethanil treatment (see Table 2). Similarly, 1 mg/L, 0.2 mg/L, and 0.04 mg/L concentrations of vaporized pyrimethanil were able to inhibit fungal sporulation in inoculated oranges having only 2.1 mm, 2.4 mm, and 2.1 mm of fungal sporulation observed on Day 2, respectively. The fungal sporulation results shown in Table 2 and FIG. 1 also indicate a dose dependent response to the vaporized pyrimethanil. Ultimately, these data demonstrate that the present method using vaporized pyrimethanil may be used to inhibit growth of plant pathogens, such as *P. digitatum*, inoculated in fruits, such as oranges.

TABLE 2

In vivo assay of vaporized pyrimethanil to inhibit *Penicillium digitatum* in oranges.

| mg/L | Water soaked Lesion (mm) | | | Fungal Sporulation (mm) | | |
| --- | --- | --- | --- | --- | --- | --- |
| | Day 0 | Day 1 | Day 2 | Day 0 | Day 1 | Day 2 |
| 1 | 0.0 | 0.0 | 0.0 | 1.8 | 2.0 | 2.1 |
| 0.2 | 0.0 | 0.0 | 1.5 | 0.6 | 0.8 | 2.4 |
| 0.04 | 0.0 | 0.0 | 0.0 | 1.1 | 1.4 | 2.1 |
| Control | 12.7 | 23.2 | 38.2 | 0.0 | 4.1 | 22.4 |

An appropriate amount of pyrimethanil to achieve a final treatment concentration of 1 mg/L, 0.2 mg/L, or 0.04 mg/L was dissolved in acetone and 100 µL of the solution was pipetted into a small glass tube. This tube was then placed inside a preheated vaporization device (0.5" OD by 6" long thermostatically heated copper tube mounted to a 0.5 L/min low flow fan) set at 60° C. for 1 minute to allow the acetone to evaporate, leaving behind the solid crystals of pyrimethanil.

Pyrimethanil was then introduced into the cabinets of the chamber through the bulkhead port by using the vaporization device as described in Example 1 set at 180° C. The chambers were then incubated at 21° C. for three (3) days. After incubation, fruits were evaluated daily for an additional 3 days at 21° C. Fruits were evaluated in order to observe disease incidence (i.e., browning) and fungal sporulation diameter (both measured in millimeters, mm).

Figure 2:
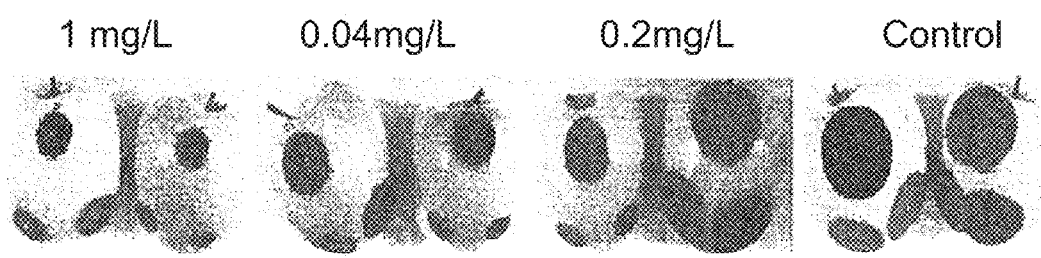
FIG. 2 shows images of *Penicillium expansum* growth after being inoculated on apples and treated with vaporized pyrimethanil.

The outcome of this in vivo experiment is summarized in Table 3 and FIG. 2. Results demonstrate that the present method comprising vaporized pyrimethanil provides good in vivo inhibition of *P. expansum* antimicrobial growth inoculated in apples. More specifically, these data indicate that vaporized pyrimethanil provides inhibition of growth of *P. expansum* causing browning and fungal sporulation in apples.

In particular, Day 3 control apples showed browning and fungal sporulation reaching 32.4 mm and 3.7 mm, respectively. However, 1 mg/L, 0.2 mg/L, and 0.04 mg/L concentrations of pyrimethanil were able to inhibit browning on apples by Day 3 to 11.4 mm, 16.2 mm, and 28.8 mm, respectively (see Table 2). Similarly, 1 mg/L, 0.2 mg/L, and 0.04 mg/L concentrations of vaporized pyrimethanil were able to inhibit fungal sporulation in inoculated apples having only 1.6 mm, 2.6 mm, and 3.1 mm of fungal sporulation observed on Day 3. The fungal sporulation results shown in Table 3 and FIG. 2 also indicate a dose dependent response of the vaporized pyrimethanil. Ultimately, these data demonstrate that the present method using vaporized pyrimethanil may be used to inhibit growth of plant pathogens, such as *P. expansum*, inoculated in fruits, such as apples.

TABLE 3

In vivo assay of vaporized pyrimethanil to inhibit *Penicillium expansum* in apples.

| Rate (mg/L) | Browning (mm) | | | | Fungal Sporulation (mm) | | | |
| --- | --- | --- | --- | --- | --- | --- | --- | --- |
| | Day 0 | Day 1 | Day 2 | Day 3 | Day 0 | Day 1 | Day 2 | Day 3 |
| 1 | 3.4 | 5.6 | 8.8 | 11.4 | 0.1 | 0.7 | 0.8 | 1.6 |
| 0.2 | 5.3 | 8.1 | 12.7 | 16.2 | 0.3 | 0.8 | 1.4 | 2.6 |
| 0.04 | 10.6 | 16.2 | 23.1 | 28.8 | 2.6 | 2.1 | 2.8 | 3.1 |
| Control | 13.0 | 19.9 | 26.0 | 32.4 | 2.1 | 2.9 | 3.8 | 3.7 |

Example 3: Vaporized Pyrimethanil Treatment on *P. Expansum* (In Vivo)

An in vivo assay was used to evaluate the ability of vaporized pyrimethanil to control pathogenic infection of apples by *Penicillium expansum*. Two apples (per repetition, in triplicate) were placed in a clamshell, and three fresh wounds were made near the equatorial region of each fruit. Each wound was then inoculated with 30 µL of 1×10$^6$ spores/mL suspension of *P. expansum*. Clamshells were then placed at the bottom of a 36-L acrylic desiccator chamber in triplicate.

Example 4: Vaporized Pyrimethanil Treatment on *B. cinerea* (In Vivo)

An in vivo assay was used to evaluate the ability of vaporized pyrimethanil to control pathogenic infection of strawberries by *Botrytis cinerea*. *B. cinerea* is a fungal pathogen known to cause gray mold infection of fruits, such as grapes and strawberries.

Eight strawberries (per repetition, in triplicate) were placed in an industry standard clamshell with the stem facing down. A fresh wound on the upwards facing tip of the fruit was then inoculated with 20 µL of 1×10$^5$ spores/mL suspension of *B. cinerea*. Clamshells were then placed at the bottom of a 36-L acrylic desiccator chamber in triplicate.

An appropriate amount of pyrimethanil to achieve a final headspace concentration of 1 mg/L, 0.3 mg/L, 0.1 mg/L, or 0.03 mg/L was dissolved in acetone and 100 µL of the solution was pipetted into a small glass tube. This tube was then placed inside a preheated vaporization device (0.5" OD by 6" long thermostatically heated copper tube mounted to a 0.5 L/min low flow fan) set at 60° C. for 1 minute to allow the acetone to evaporate, leaving behind the solid crystals of pyrimethanil.

Pyrimethanil was then introduced into the cabinets of the chamber through the bulkhead port by using the vaporization device as described in Example 1 set at 180° C. The chambers were then incubated at 21° C. for three (3) days. After incubation, fruits were evaluated daily for an additional 3 days at 21° C. Fruits were evaluated in order to observe percentage of disease incidence (%) and severity of disease. Disease severity was rated on a scale ranging from 0 to 4, where "0" indicated no disease severity, "1" indicated minimal disease severity, "2" indicated medium disease severity, "3" indicated high disease severity, and "4" indicated exceptionally high disease severity.

Figure 3:
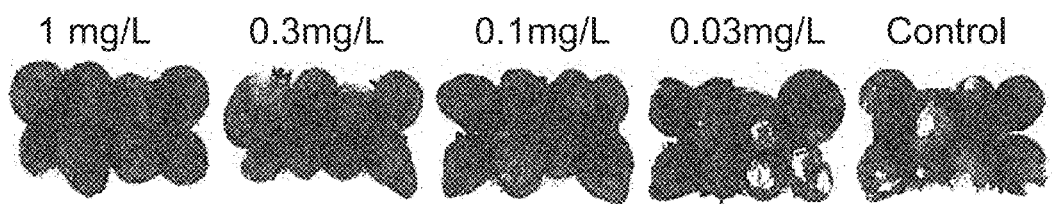
FIG. 3 shows images of *Botrytis cinerea* growth after being inoculated on strawberries and treated with vaporized pyrimethanil.

The outcome of this in vivo experiment is summarized in Table 4 and FIG. 3. Results demonstrate that the present method comprising vaporized pyrimethanil provides in vivo inhibition of *B. cinerea* antimicrobial growth inoculated in strawberries. More specifically, these data indicate that vaporized pyrimethanil inhibits *B. cinerea* causing gray mold disease incidence and severity in strawberries.

In particular, Day 3 control strawberries showed disease incidence and severity of 100% and 2.7, respectively. However, 1 mg/L and 0.3 mg/L concentrations of pyrimethanil were able to inhibit gray mold incidence in strawberries by Day 3 to 91.7% and 95.8%, respectively (see Table 4). Similarly, 1 mg/L, 0.3 mg/L, 0.1 mg/L, and 0.03 mg/L concentrations of vaporized pyrimethanil were able to inhibit gray mold severity on Day 3 in inoculated strawberries to 1.0, 1.1, 1.7, and 2.1, respectively. The gray mold incidence and severity shown in Table 4 and FIG. 3 also indicate a dose dependent response to the vaporized pyrimethanil. Ultimately, these data demonstrate that the present method using vaporized pyrimethanil may be used to inhibit growth of plant pathogens, such as *B. cinerea*, inoculated in fruits, such as strawberries.

standard, 1-pint clamshell with the stem-end facing up. A fresh wound was placed on the grape with a push pin, and the wound was then inoculated with 20 µL of $1 \times 10^5$ spores/mL suspension of *B. cinerea*. Clamshells were then placed at the bottom of a 36-L acrylic desiccator chamber in triplicate.

An appropriate amount of pyrimethanil to achieve a final headspace concentration of 0.3 mg/L, 0.1 mg/L, 0.03 mg/L, or 0.01 mg/L was dissolved in acetone and 100 µL of the solution was pipetted into a small glass tube. This tube was then placed inside a preheated vaporization device (0.5" OD by 6" long thermostatically heated copper tube mounted to a 0.5 L/min low flow fan) set at 60° C. for 1 minute to allow the acetone to evaporate, leaving behind the solid crystals of pyrimethanil.

Pyrimethanil was then introduced into the cabinets of the chamber through the bulkhead port by using the vaporization device as described in Example 1 set at 180° C. The chambers were then incubated at 21° C. for three (3) days. After incubation, fruits were evaluated daily for an additional 3 days at 21° C. Fruits were evaluated in order to observe percentage of disease incidence (%) and severity of disease. Disease severity was rated on a scale ranging from 0 to 4, where "0" indicated no disease severity, "1" indicated minimal disease severity, "2" indicated medium disease severity, "3" indicated high disease severity, and "4" indicated exceptionally high disease severity.

Figure 4:
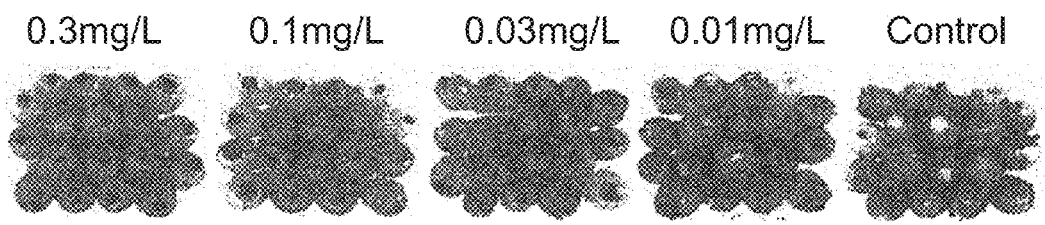
FIG. 4 shows images of *Botrytis cinerea* growth after being inoculated on Table grapes and treated with vaporized pyrimethanil.

The outcome of this in vivo experiment is summarized in Table 5 and FIG. 4. Results demonstrate that the present method comprising vaporized pyrimethanil provides in vivo inhibition of *B. cinerea* antimicrobial growth inoculated in grapes. More specifically, these data indicate that vaporized pyrimethanil inhibits *B. cinerea* causing gray mold disease incidence and severity in grapes.

In particular, Day 3 control grapes showed disease incidence and severity of 100% and 3.9, respectively. A 0.3 mg/L concentration of pyrimethanil was able to inhibit all but 16.7% of gray mold incidence in grapes on day 0 (see Table 5). In addition, 0.3 mg/L, 0.1 mg/L, 0.03 mg/L, or 0.01 mg/L concentrations of vaporized pyrimethanil were able to inhibit gray mold severity on Day 3 in inoculated grapes to

TABLE 4

In vivo assay of vaporized pyrimethanil to inhibit *Botrytis cinerea* in strawberries.

| | Gray Mold incidence (%) | | | | Gray Mold severity (0-4) | | | |
|---|---|---|---|---|---|---|---|---|
| Rates mg/L | Day 0 | Day 1 | Day 2 | Day 3 | Day 0 | Day 1 | Day 2 | Day 3 |
| Control | 95.8 | 95.8 | 100.0 | 100.0 | 1.1 | 1.6 | 2.1 | 2.7 |
| 0.03 | 79.2 | 87.5 | 91.7 | 100.0 | 0.8 | 1.3 | 1.7 | 2.1 |
| 0.1 | 70.8 | 79.2 | 83.3 | 100.0 | 0.6 | 0.8 | 1.2 | 1.7 |
| 0.3 | 66.7 | 75.0 | 73.8 | 95.8 | 0.4 | 0.5 | 0.8 | 1.1 |
| 1 | 66.7 | 70.8 | 69.6 | 91.7 | 0.3 | 0.4 | 0.6 | 1.0 |

Example 5: Vaporized Pyrimethanil Treatment on *B. cinerea* (In Vivo)

An in vivo assay was used to evaluate the ability of vaporized pyrimethanil to control pathogenic infection of Table grapes by *Botrytis cinerea*. Fifteen (15) Table grapes (per repetition, in triplicate) were placed in an industry 1.3, 1.8, 3.4, and 3.6, respectively. The gray mold incidence and severity shown in Table 5 and FIG. 4 also indicate a dose dependent response to the vaporized pyrimethanil. Ultimately, these data demonstrate that the present method using vaporized pyrimethanil may be used to inhibit growth of plant pathogens, such as *B. cinerea*, inoculated in fruits, such as grapes.

TABLE 5

In vivo assay of vaporized pyrimethanil to inhibit *Botrytis cinerea* in grapes.

|  | Gray Mold Incidence (%) | | | | Gray Mold Severity (0-4) | | | |
| --- | --- | --- | --- | --- | --- | --- | --- | --- |
| Rate (mg/L) | Day 0 | Day 1 | Day 2 | Day 3 | Day 0 | Day 1 | Day 2 | Day 3 |
| Control | 100.0 | 100.0 | 100.0 | 100.0 | 2.5 | 2.8 | 2.9 | 3.9 |
| 0.01 | 100.0 | 100.0 | 100.0 | 100.0 | 1.6 | 2.0 | 2.0 | 3.6 |
| 0.03 | 100.0 | 100.0 | 100.0 | 100.0 | 1.4 | 2.0 | 2.0 | 3.4 |
| 0.1 | 94.4 | 98.1 | 98.1 | 98.1 | 0.5 | 0.7 | 1.1 | 1.8 |
| 0.3 | 16.7 | 94.4 | 94.4 | 100.0 | 0.1 | 0.5 | 0.8 | 1.3 |

Example 6: Vaporized Pyrimethanil Treatment on *B. cinerea* (In Vivo)

An in vivo assay was used to evaluate the ability of vaporized pyrimethanil to control pathogenic infection of blueberries by *Botrytis cinerea*. Twenty-seven (27) blueberries (per repetition, in triplicate) were placed in an industry standard, 1-pint PET clamshell with the stem-end facing up. A fresh wound was placed in each blueberry with a push pin, and the wound was then inoculated with 20 µL of $1 \times 10^5$ spores/mL suspension of *B. cinerea*. Clamshells were then placed at the bottom of a 36 L acrylic desiccator chamber in triplicate.

An appropriate amount of pyrimethanil to achieve a final headspace concentration of 0.3 mg/L, 0.1 mg/L, 0.03 mg/L, or 0.01 mg/L was dissolved in acetone and 100 µL of the solution was pipetted into a small glass tube. This tube was then placed inside a preheated vaporization device (0.5" OD by 6" long thermostatically heated copper tube mounted to a 0.5 L/min low flow fan) set at 60° C. for 1 minute to allow the acetone to evaporate, leaving behind the solid crystals of pyrimethanil.

Pyrimethanil was then introduced into the cabinets of the chamber through the bulkhead port by using the vaporization device as described in Example 1 set at 180° C. The chambers were then incubated at 21° C. for three (3) days. After incubation, fruits were evaluated daily for an additional 3 days at 21° C. Fruits were evaluated in order to observe percentage of disease incidence (%) and severity of disease. Disease severity was rated on a scale ranging from 0 to 4, where "0" indicated no disease severity, "1" indicated minimal disease severity, "2" indicated medium disease severity, "3" indicated high disease severity, and "4" indicated exceptionally high disease severity.

Figure 5:
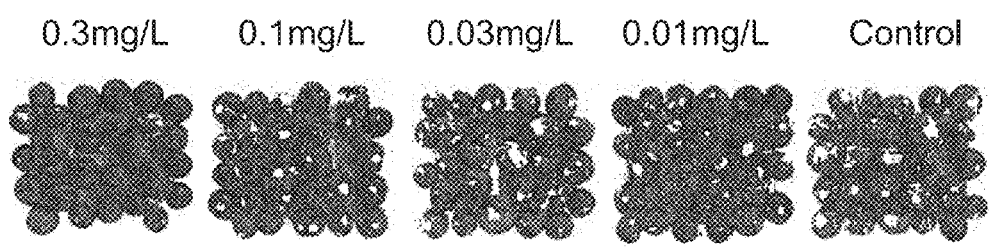
FIG. 5 shows images of *Botrytis cinerea* growth after being inoculated on blueberries and treated with vaporized pyrimethanil.
Figure 6:
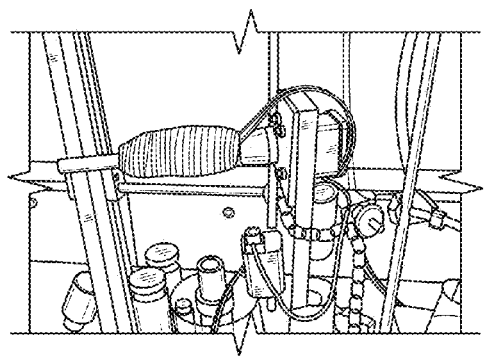
FIG. 6 shows an image of the heating device comprising a heating element or a sublimation unit.
Figure 7:
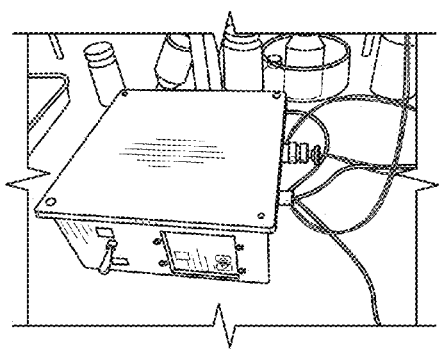
FIG. 7 shows an image of an external power source.
Figure 8:
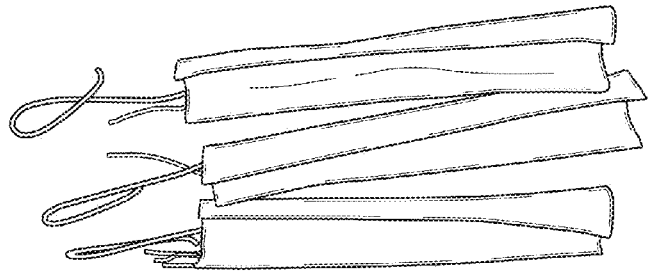
FIG. 8 shows an image of fabric or cloth carrier for the active ingredient.
Figure 9:
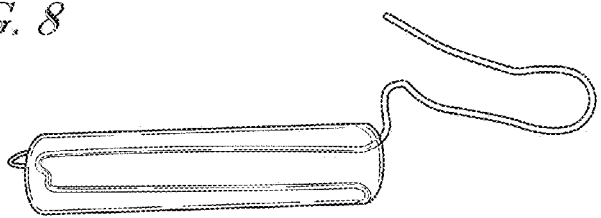
FIG. 9 shows an image of a glass tube carrier for the active ingredient.
Figure 10:
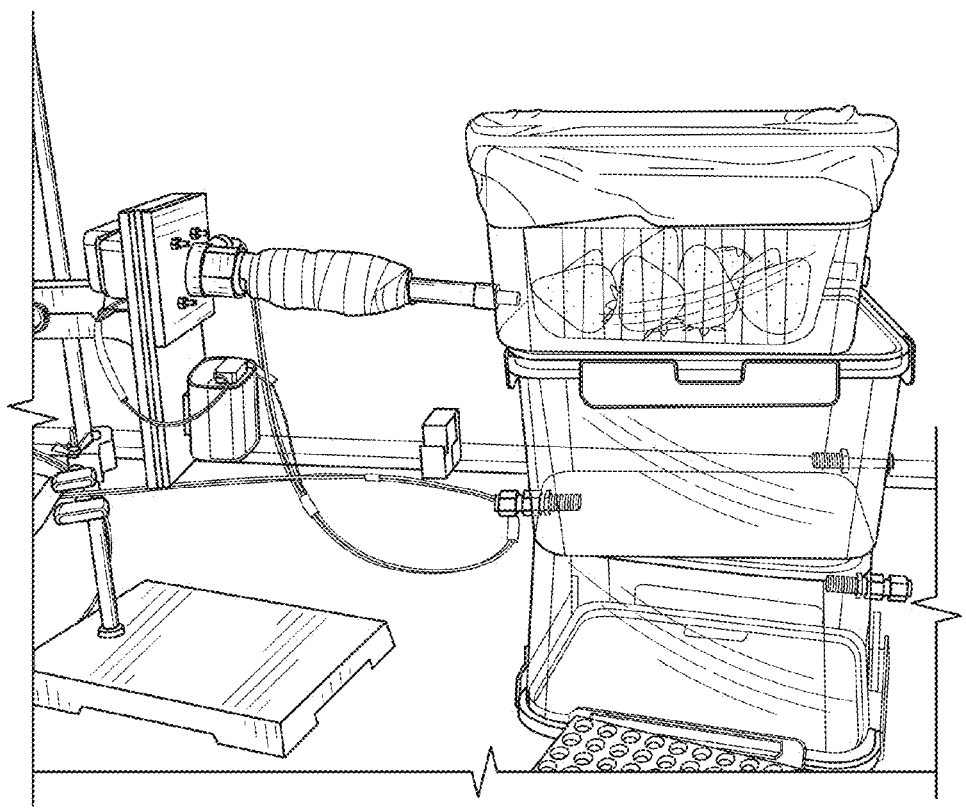
FIG. 10 shows an image of a heating device penetrating a chamber (i.e., a mini-pallet) comprising strawberries.

The outcome of this in vivo experiment is summarized in Table 6 and FIG. 5. Results demonstrate that the present method comprising vaporized pyrimethanil provides in vivo inhibition of *B. cinerea* antimicrobial growth inoculated in blueberries. More specifically, these data indicate that vaporized pyrimethanil inhibits *B. cinerea* causing gray mold disease incidence and severity in blueberries.

In particular, Day 3 control grapes showed disease incidence and severity of 98.8% and 2.1, respectively. However, 0.3 mg/L concentration of pyrimethanil was able to inhibit gray mold incidence in blueberries to 52.0% by Day 3 (see Table 6). In addition, 0.3 mg/L, 0.1 mg/L, and 0.03 mg/L concentrations of vaporized pyrimethanil were able to inhibit gray mold severity on Day 3 in inoculated blueberries to 0.3, 1.7, and 1.7, respectively. No inhibition of gray mold occurred with the 0.01 mg/L concentration of pyrimethanil.

The gray mold incidence and severity shown in Table 6 and FIG. 5 also indicate a dose dependent response to the vaporized pyrimethanil. Ultimately, these data demonstrate that the present method using vaporized pyrimethanil may be used to inhibit growth of plant pathogens, such as *B. cinerea*, inoculated in fruits, such as blueberries.

TABLE 6

In vivo assay of vaporized pyrimethanil to inhibit *Botrytis cinerea* in blueberries.

|  | Gray Mold Incidence (%) | | | | Gray Mold Severity (0-4) | | | |
| --- | --- | --- | --- | --- | --- | --- | --- | --- |
| Rate (mg/L) | Day 0 | Day 1 | Day 2 | Day 3 | Day 0 | Day 1 | Day 2 | Day 3 |
| Control | 96.3 | 98.8 | 98.8 | 98.8 | 0.9 | 1.2 | 1.6 | 2.1 |
| 0.01 | 92.6 | 96.3 | 98.8 | 98.8 | 0.9 | 1.1 | 1.4 | 2.1 |
| 0.03 | 82.7 | 97.5 | 97.5 | 97.5 | 0.7 | 1.1 | 1.3 | 1.7 |
| 0.1 | 64.2 | 87.8 | 94.8 | 94.6 | 0.5 | 0.9 | 1.1 | 1.7 |
| 0.3 | 22.2 | 33.8 | 51.2 | 52.0 | 0.2 | 0.2 | 0.3 | 0.3 |

Example 7: A Heating Device to Vaporize Antimicrobial Treatment

This example relates to the heating device of the present disclosure (see FIGS. 6-10). The heating device comprises a heating element surrounding a heating chamber or container, such as a copper tube (see FIGS. 6 and 10). The heating device also comprises a power source (see FIG. 7).

The heating element is capable of producing high temperatures needed to achieve the vaporization temperature of a technical solid active ingredient, such as pyrimethanil. The active ingredient is placed into the heating chamber in a number of possible ways, such as placed into a glass tube (see FIG. 9) that is inserted into the heating chamber of the device. The active ingredient solution may also be placed directly on the heated surface using a pipette, syringe, or similar. Alternatively, the solid active ingredient may be dissolved with a volatile solvent, and the desired amount of dissolved active may be placed in or on a solid carrier, such as cotton or a non-flammable absorbent material (see FIG. 8).

A source of low volume air flow, such as a fan, is also comprised by the heating device (not shown). The air flow source (e.g., a fan) will push air though the heating chamber comprising the vaporized active ingredient and through the heating device and further through one or more orifices located at the distal end of the heating device. The one or more orifices on the distal end of the heating device may penetrate a chamber (see FIGS. 10-11) comprising fruits, flowers, or vegetables to be treated as described in Example 1-6.

Example 8: Melting Point of Pyrimethanil Compound

This example relates to experiments performed to determine the melting temperatures of pyrimethanil technical compounds and fungicide samples. In the present example, pyrimethanil compounds from China (compound 1) and Europe (compound 2) were analyzed by Differential Scanning calorimetry (DSC). The pyrimethanil compounds were run in a Tzero™ hermetically sealed aluminum pan on the Q2000 DSC instrument (TA Instruments) equipped with a liquid nitrogen cooling system, and using standard DSC test methods as follows: equilibrate at 0° C., isothermal for 5 minutes, ramp at 10° C. per minute to 140° C., and end method.

Figure 12:
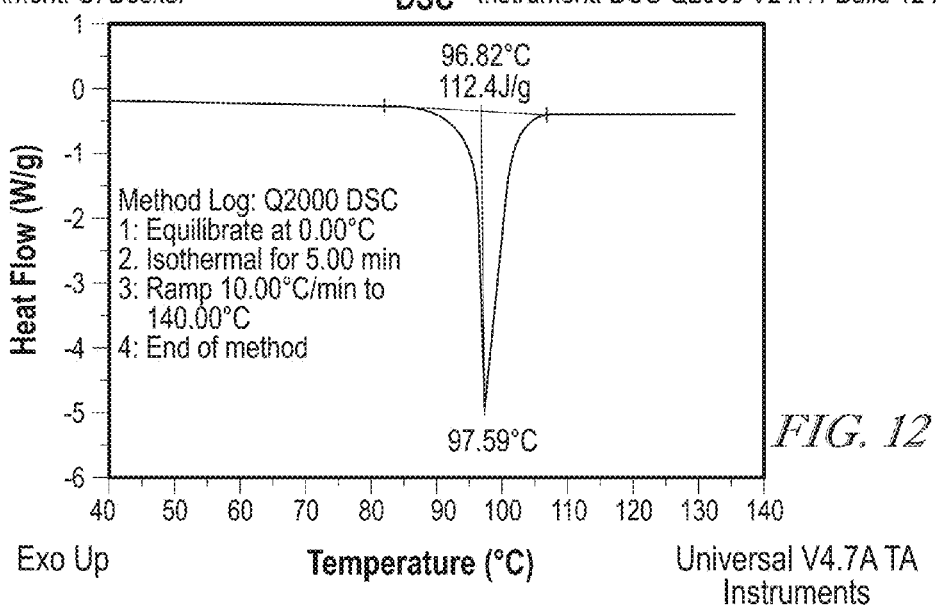
FIG. 12 shows a DSC isothermal curve of the melting temperature of a pyrimethanil compound 1.
Figure 13:
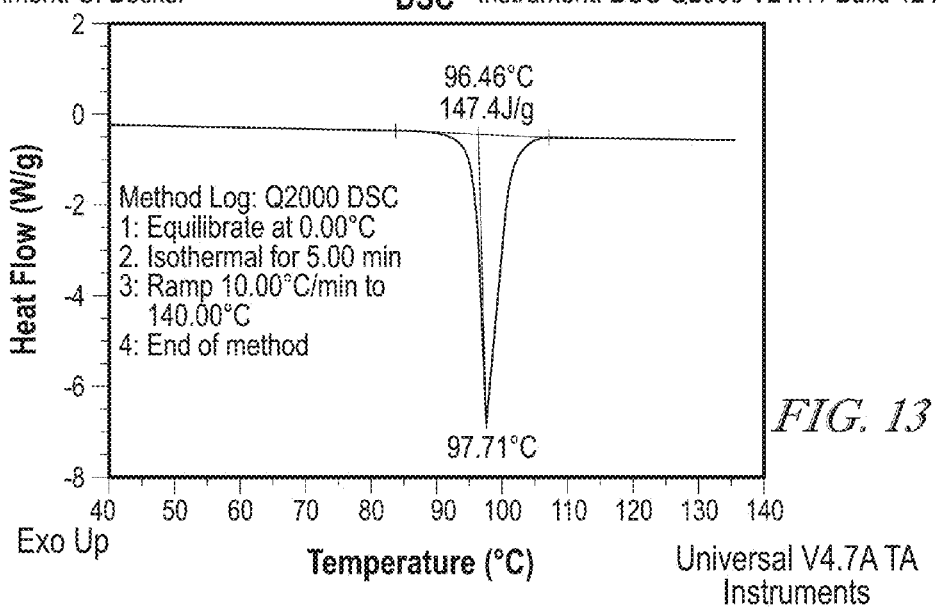
FIG. 13 shows a DSC isothermal curve of the melting temperature of pyrimethanil compound 2.

The results of this example for the Chinese (CH; compound 1) and European (EU; compound 2) pyrimethanil compounds are shown in FIGS. 12 and 13, respectively. As shown in FIG. 12, the melting temperature of pyrimethanil compound 1 ranged from about 96.8° C. to about 97.6° C., and had a heat of fusion of about 112.4 J/g. FIG. 13 shows that the melting temperature of pyrimethanil compound 2 ranged from about 96.5° C. to about 97.7° C., and had a heat of fusion of about 147.4 J/g. Thus, FIGS. 12 and 13 confirm that the melting temperature of pyrimethanil ranges from about 96° C. to about 98° C. However, since the heats of fusion profiles of the two pyrimethanil compounds are not similar (112.4 J/g for pyrimethanil compound 1 and 147.4 J/g for pyrimethanil compound 2), it is undetermined whether the pyrimethanil compounds 1 and 2 are identical.

Example 9: Degradation Temperature of Pyrimethanil Compound

This example relates to experiments performed to determine the degradation temperatures of pyrimethanil technical compounds and fungicide samples. In the present example, pyrimethanil compounds from China (compound 1) and Europe (compound 2) were analyzed by Thermo Gravity Analysis (TGA). The pyrimethanil samples were run in both air and nitrogen atmospheres on the Q5000 TGA instrument (TA Instruments) equipped in open platinum pans, and using standard TGA test methods as follows: select gas 1 and 2, data storage on, ramp at 10° C. per minute to 300° C., data storage off, and end method. An isothermal method was also performed according to standard methods.

Figure 14A:
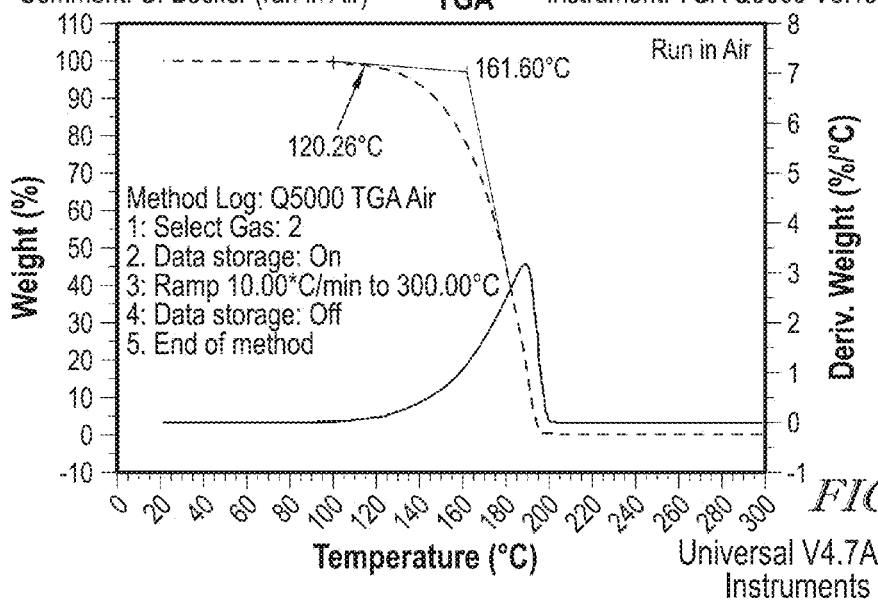
FIG. 14A shows a TGA isothermal curve run in air of the degradation temperature of pyrimethanil compound 1.
Figure 14B:
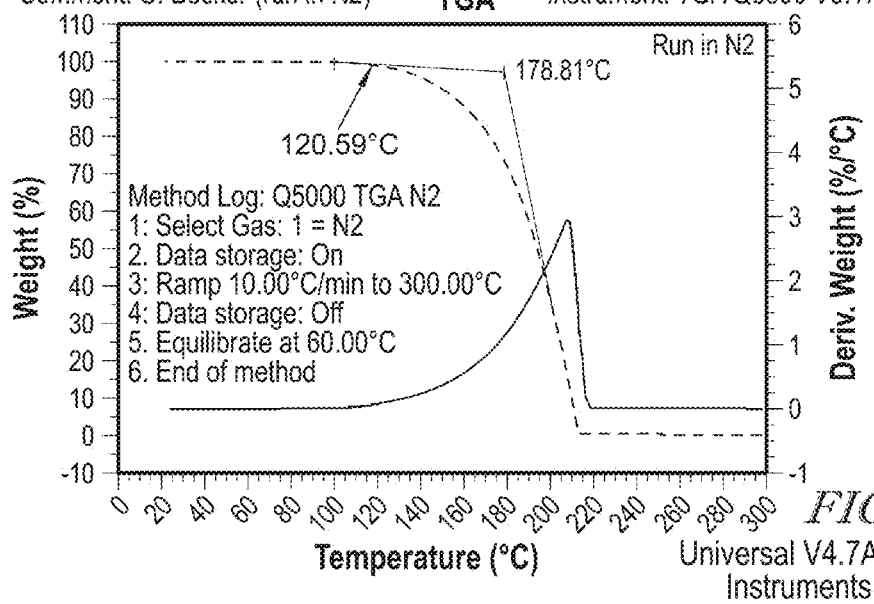
FIG. 14B shows a TGA isothermal curve run in nitrogen of the degradation temperature of pyrimethanil compound 1.
Figure 15A:
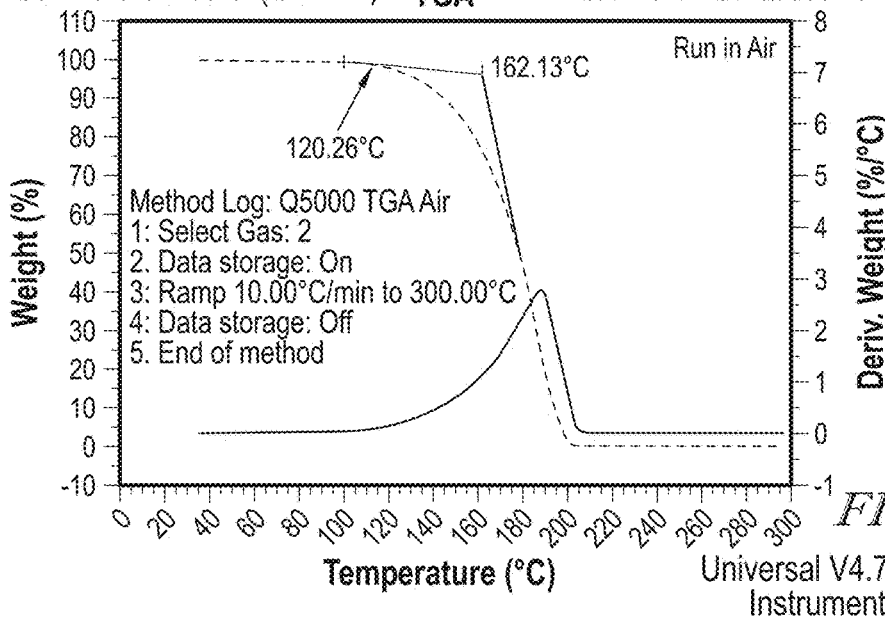
FIG. 15A shows a TGA isothermal curve run in air of the degradation temperature of pyrimethanil compound 2.
Figure 15B:
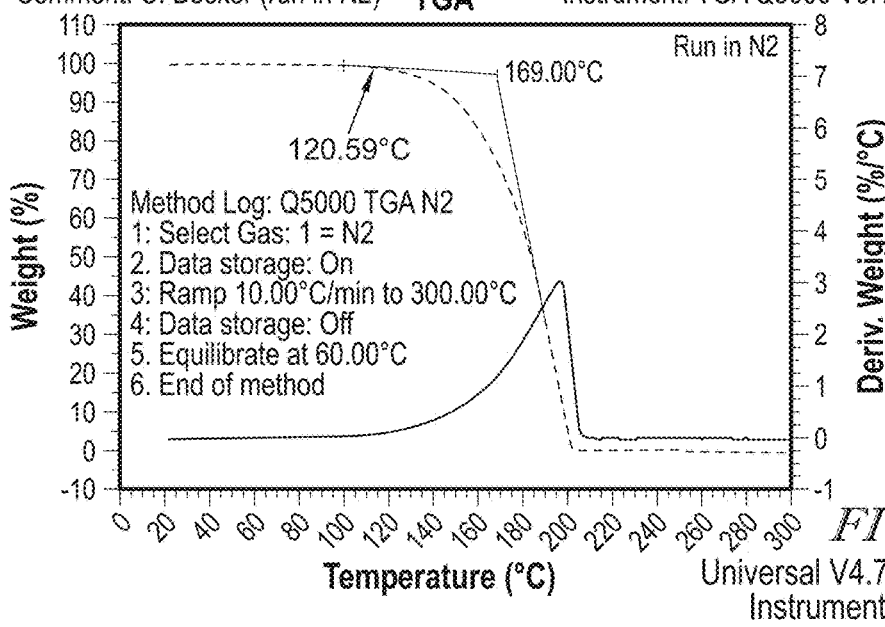
FIG. 15B shows a TGA isothermal curve run in nitrogen of the degradation temperature of a pyrimethanil compound 2.

The results of this example for the Chinese (CH; compound 1) pyrimethanil compound in air and nitrogen are shown in FIGS. 14A and 14B, respectively. The results of this example for the European (EU; compound 2) pyrimethanil compound in air and nitrogen are shown in FIGS. 15A and 15B, respectively. As shown in FIGS. 14-15, degradation of both of the pyrimethanil compounds began at about 120.3° C. in air and at about 120.6° C. in nitrogen, and was complete at about 200° C. in both air and nitrogen. Thus, FIGS. 14-17 demonstrate that the degradation temperature of pyrimethanil ranges from about 120° C. to about 200° C.

Example 10: Degradation by Evaporation of Pyrimethanil Compound

This example relates to experiments performed to determine if degradation of pyrimethanil technical compounds observed at high temperatures was due to evaporation. In the present example, seven milligrams (7 mg) of pyrimethanil compounds 1 and 2 were analyzed in air by Thermo Gravity Analysis-Mass Spectrometry (TGA-MS). The pyrimethanil samples were loaded onto a TGA platinum pan of the Q5000 TGA instrument (TA instruments) and using standard TGA test methods as follows: select gas 2 (air), data storage on, ramp at 5° C. per minute to 100° C., isothermal for 180 mins, data storage off, equilibrate at 60° C., and end method. An isothermal method was also performed according to standard methods.

Figure 16A:
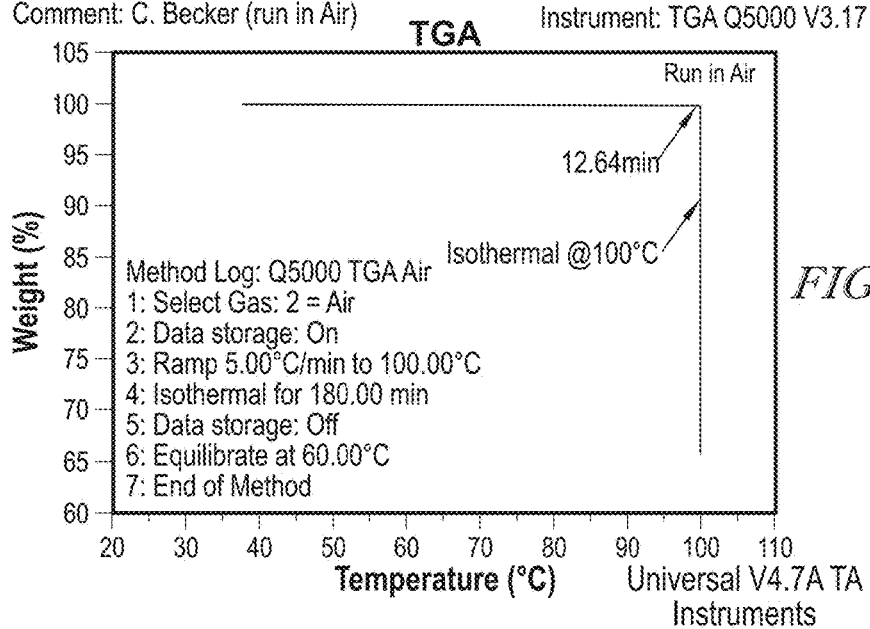
FIG. 16A shows a TGA-MS isothermal curve run in air of the degradation temperature of pyrimethanil compound 1.
Figure 16B:
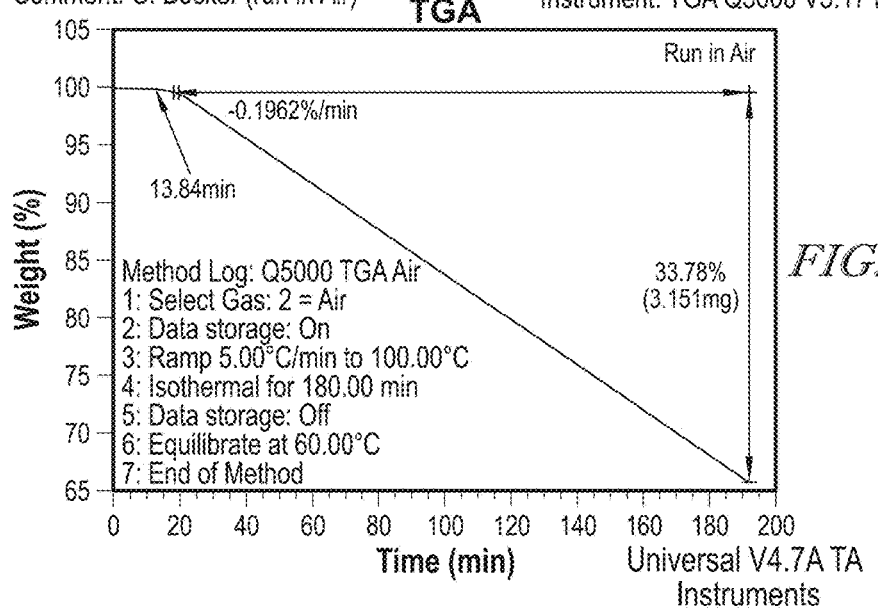
FIG. 16B shows a TGA-MS isothermal curve analysis of the degradation temperature of a pyrimethanil compound 1.
Figure 17A:
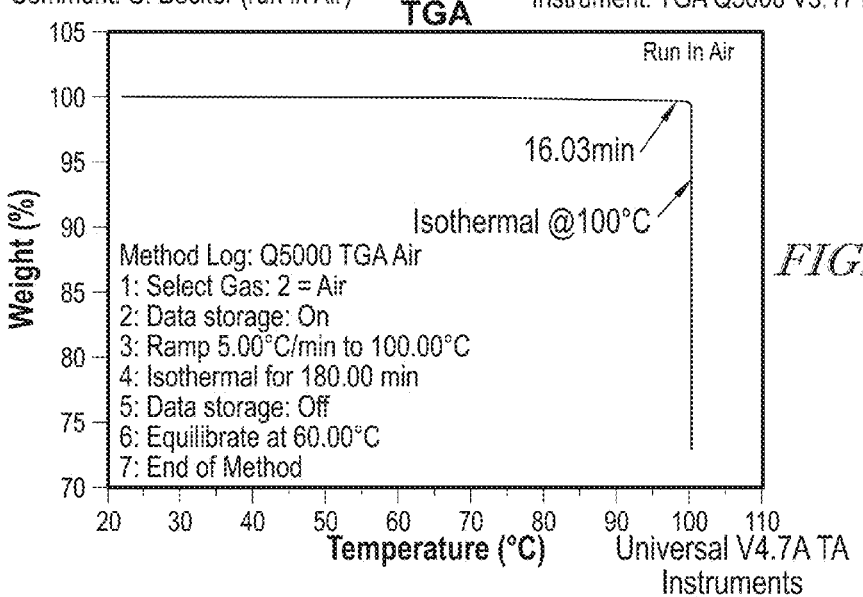
FIG. 17A shows a TGA-MS isothermal curve run in air of the degradation temperature of pyrimethanil compound 2.
Figure 17B:
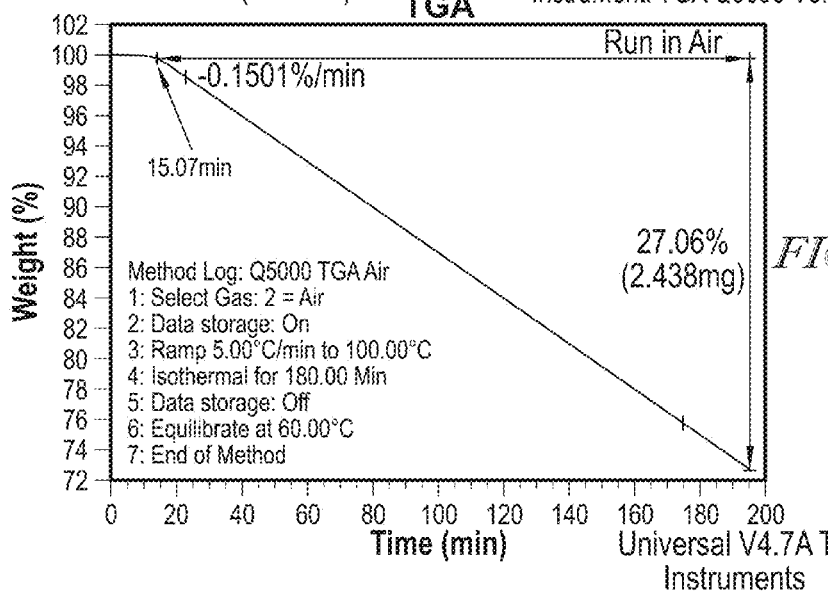
FIG. 17B shows a TGA-MS isothermal curve analysis of the degradation temperature of a pyrimethanil compound 2.

The TGA furnace was closed and purged with helium, then heated from room temperature to about 300° C. at 10° C. per minute. The effluent from the TGA furnace was transferred to a mass spectrometer through a heated interface and transfer line, which had a maximum temperature of 300° C. An isothermal method was also performed according to standard methods. The results of this example for the Chinese (CH) pyrimethanil compound 1 are shown in FIGS. 16A and 16B. The results of this example for the European (EU) pyrimethanil compound 2 are shown in FIGS. 17A and 17B.

Figure 18:
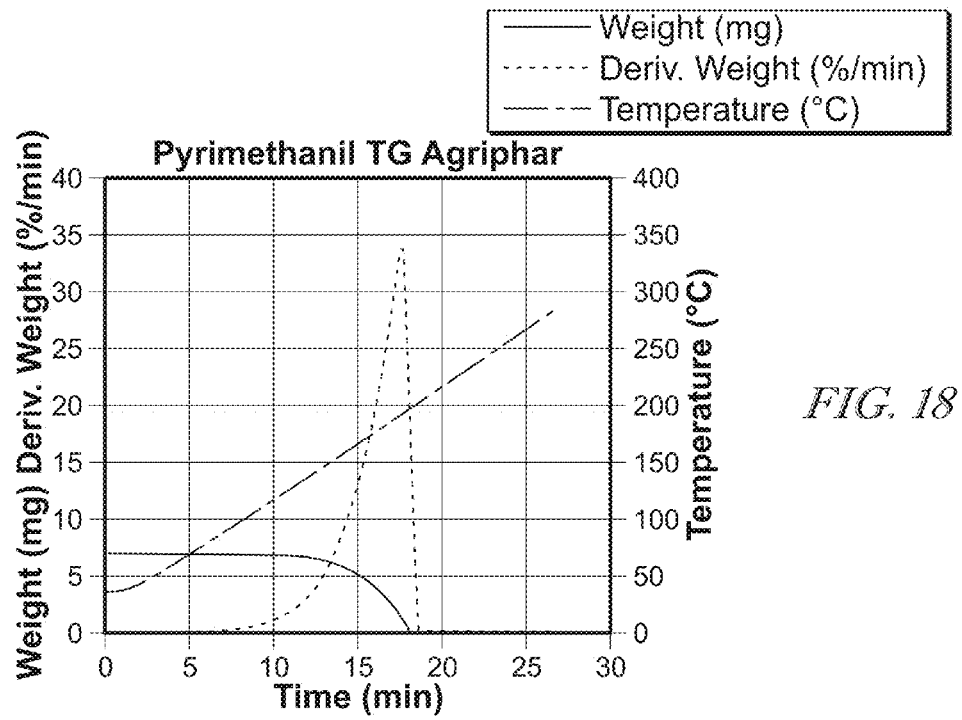
FIG. 18 shows a weight loss rate curve for pyrimethanil compound 2.
Figure 19:
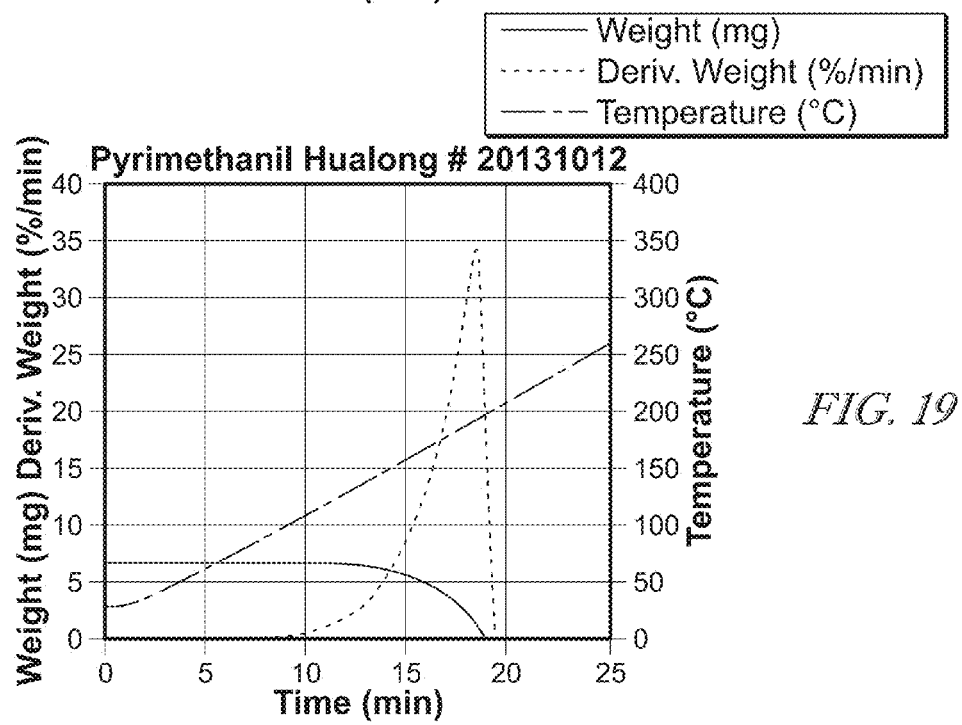
FIG. 19 shows a weight loss rate curve for pyrimethanil compound 1.

FIGS. 18 and 19 show weight loss rate curves for pyrimethanil compounds 2 and 1, respectively. FIGS. 18 and 19 demonstrate that the two pyrimethanil compounds are very similar. In fact, the shape of the weight loss rate curves and the absence of mass spectral variation over the range of observed weight loss evidence that the loss of active compound is occurring due to an evaporation process. Further, these data indicate that the pyrimethanil material is too volatile to decompose at atmospheric pressure. Thus, the onset of thermal decomposition of the pyrimethanil compound of the present disclosure likely requires a closed or pressurized device.

Figure 20:
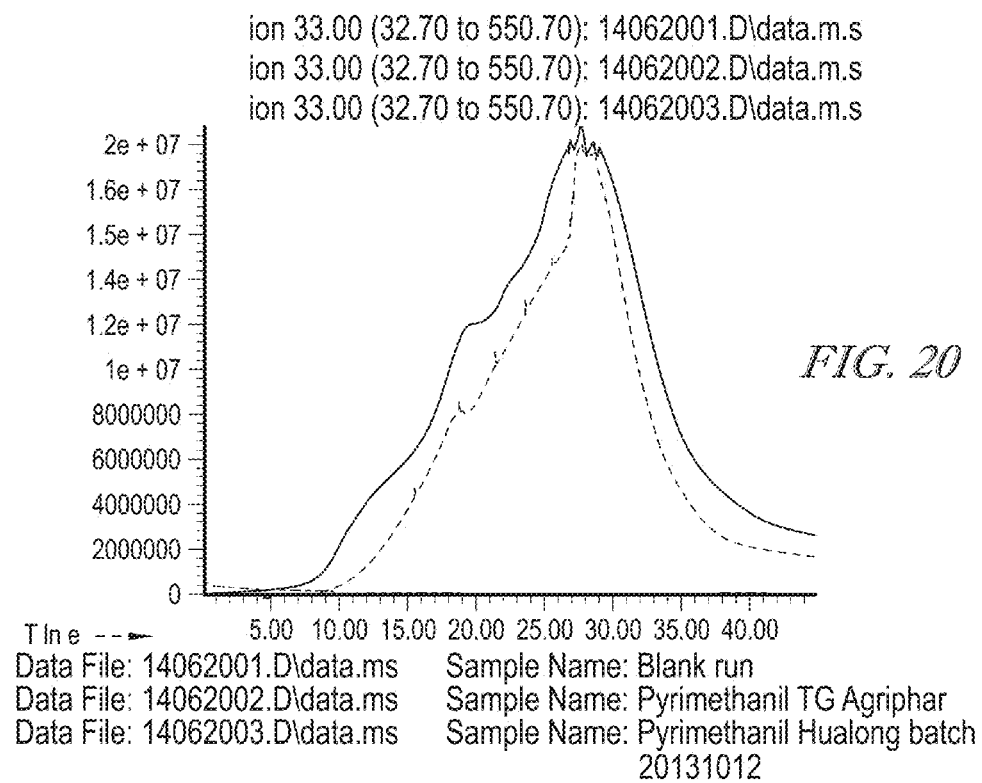
FIG. 20 shows a total ion thermogram comparison of the mass spectra of pyrimethanil compounds 1 and 2.
Figure 21:
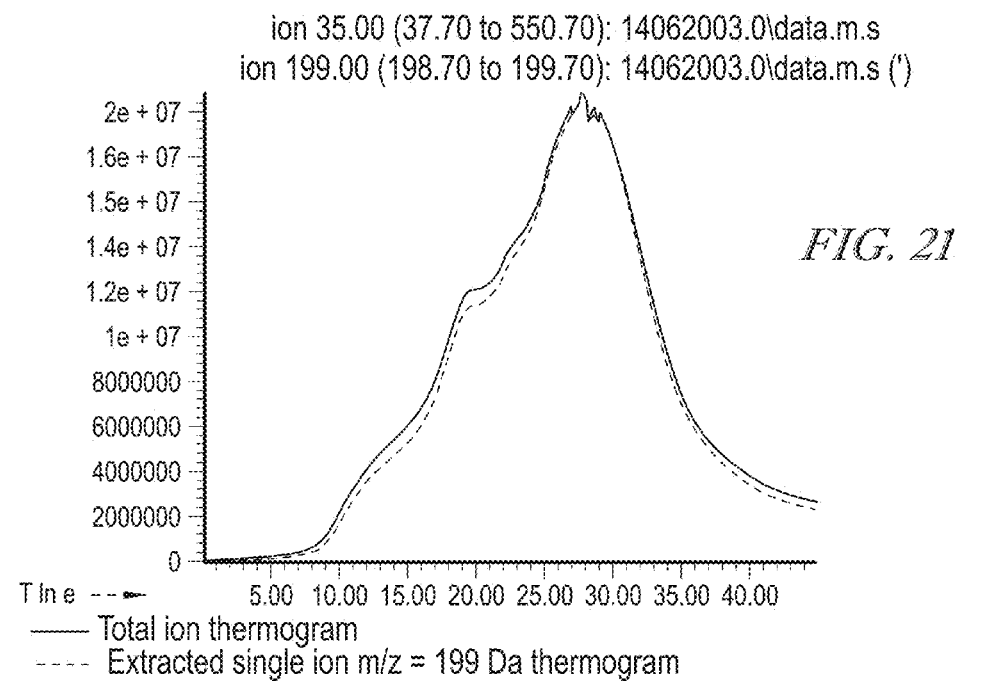
FIG. 21 shows a total ion thermogram comparison of the total ion and molecular ion profiles of pyrimethanil compounds 1 and 2.

FIG. 20 shows a comparison of the total ion thermograms of the two tested pyrimethanil compounds. The total ion thermograms of the active compounds 1 and 2 are very similar to their respective corresponding weight loss curves shown in FIGS. 18 and 19. FIG. 21 shows the evolution profile of the total ion and molecular ion thermograms of the two pyrimethanil compounds.

FIGS. 20 and 21 demonstrate that the pyrimethanil compounds overlap perfectly indicating the absence of any significant molecular changes during the 300° C. thermal event. Spectra taken at various retention times confirm the absence of detectable chemical degradation of the pyrimethanil compounds. Thus, FIGS. 20-21 demonstrate the unexpected results that the tested pyrimethanil compounds do not undergo significant molecular or chemical degradation in response to thermal events having temperature of up to 300° C., which enables the ability of the present pyrimethanil compounds to volatilize at high temperatures for use in vaporized treatments of plants and plant parts. These data are surprising and unexpected in light of the prior art, which indicates that pyrimethanil compounds begin to degrade at temperatures as low as about 189.5° C.

Example 11: Drenching Versus Vaporizing Methods of Treating Fruit

An in vivo assay was used to evaluate the ability of vaporized pyrimethanil to control pathogenic infection of apples by *Penicillium expansum* as compared to drenching methods of apple treatment. Vaporized treatments of apples were performed as previous described in Examples 1-6, with the exception of using a 1 m wide×1 m high×8 m deep tunnel (see FIG. 11). An appropriate amount of pyrimethanil to achieve a final vaporized treatment concentration/rate of 0.125 mg/L, 0.5 mg/L, or 2 mg/L was prepared. In addition, drenching treatments comprising a final concentration of 125 mg/L, 500 mg/L, and 2000 mg/L of pyrimethanil active ingredient were also prepared. Fruits were stored for nine weeks at 1° C., and evaluated in order to observe and/or determine the area of browning on the fruit (see FIG. 22) and the percent of browning inhibition (see Table 7).

Figure 22:
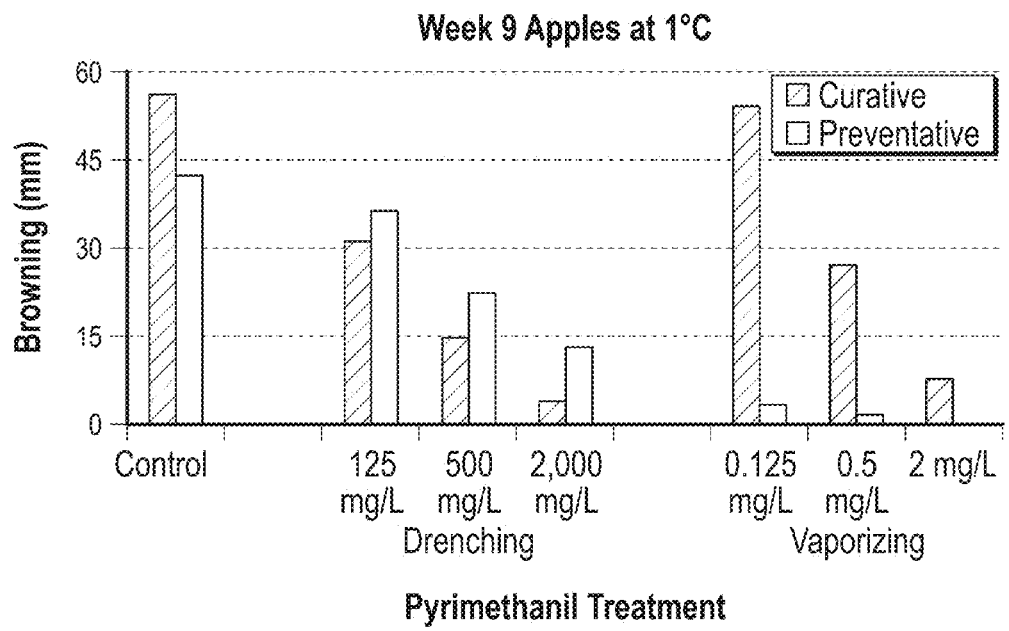
FIG. 22 shows a bar graph comparing the effect on browning of apples treated with pyrimethanil applied using a drenching method versus a vaporized method.

Results demonstrate that the present method comprising vaporized pyrimethanil provides better in vivo inhibition of *P. expansum* antimicrobial growth inoculated in apples as compared to apples that were drenched with even higher concentrations of liquid pyrimethanil compound. FIG. 22 demonstrates that apples treated in a preventative manner with vaporized pyrimethanil had less area (mm) of browning than did those apples treated by drenched pyrimethanil. In addition, Table 7 indicates that lower concentrations of the vaporized pyrimethanil had a higher percent inhibition in apples than did the higher concentrations of drenched pyrimethanil concentrations.

These data indicate that vaporized pyrimethanil provides a higher percent inhibition of growth of *P. expansum* causing browning in apples, than apples treated by drenching. Ultimately, these data demonstrate that the present method using vaporized pyrimethanil may be better and less costly method to inhibit growth of plant pathogens, such as *P. expansum*, inoculated in fruits (e.g., apples) as compared to more traditional methods of treatment, such as drenching.

TABLE 7

Drenching vs. Vaporizing Treatments of Apples

| Type | Treatment Rate (mg/L) | Apple PYR residue (ppm) | Percent (%) Inhibition of Internal Browning |
|---|---|---|---|
| VAPOR | 2 | 7.99 | 100 |
|  | 0.5 | 3.89 | 96 |
| DRENCH | 2,000 | 3.55 | 69 |
|  | 500 | 3.2 | 47 |

Example 12: Fogging Versus Vaporizing Methods of Treating Fruit

Figure 11:
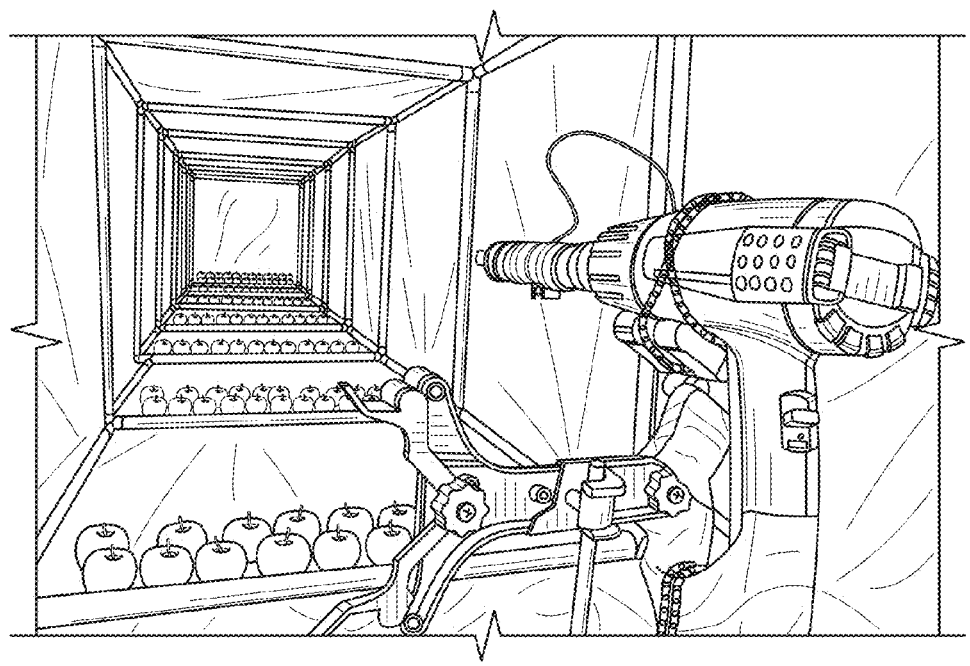
FIG. 11 shows an image of a heating device for technical vaporization application of apples in a chamber (i.e., a tunnel) that is 1 m×1 m×8 m in size.
Figure 23:
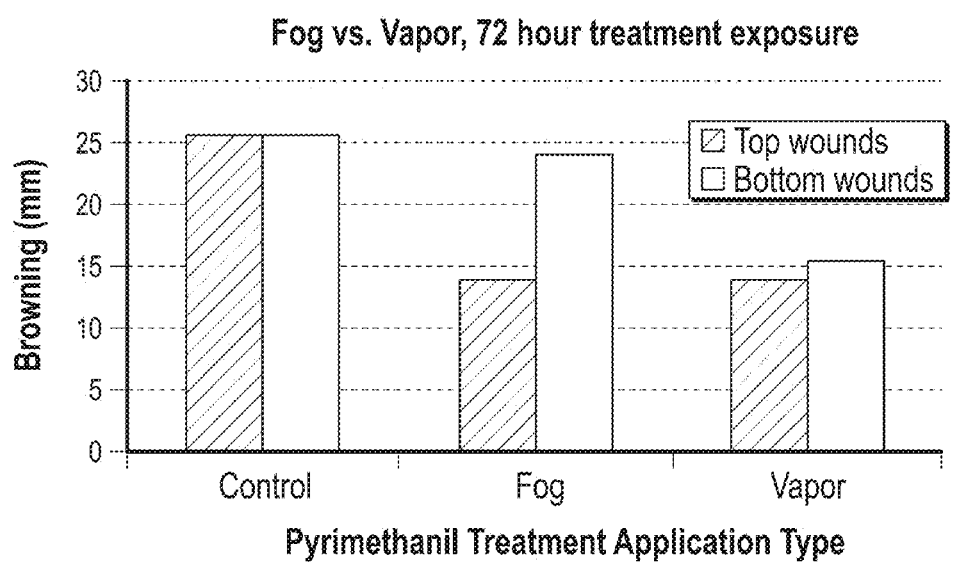
FIG. 23 shows a bar graph comparing the effect on browning of the top wounds and the bottom wounds of apples treated with pyrimethanil applied using a fogging method versus a vaporized method.

An in vivo assay was used to evaluate the ability of vaporized pyrimethanil to control pathogenic infection of apples by *Penicillium expansum* as compared to fogging methods of apple treatment. Vaporized treatments of apples were performed as previous described in Examples 1-6, with the exception of using a 1 m wide×1 m high×8 m deep tunnel (FIG. 11). A 2.66 g amount of pyrimethanil was either fogged or vaporized into the tunnel. Fruits were exposed to the treatment for 72 hours at 21° C., and then removed from the tunnel and evaluated 4 days after removal in order to observe and/or determine the area of browning wounds at the top and bottom of the fruit (see FIG. 23).

Results demonstrate that the present method comprising vaporized pyrimethanil provides better in vivo inhibition of *P. expansum* antimicrobial growth inoculated in apples as compared to apples that were fogged with pyrimethanil compound. While apples treated with vaporized pyrimethanil had comparable browning on the top of the fruit as apples that were fogged, FIG. 23 demonstrates that apples treated with vaporized pyrimethanil had much less area (mm) of browning at the bottom of the fruit than did those apples treated by fogged pyrimethanil.

These data indicate that vaporized pyrimethanil provides a better treatment method of growth of *P. expansum* causing browning in apples, than apples treated by fogging. In particular, the data provided herein demonstrates that the claimed vaporization treatment technique is better to treat the full fruit, including the bottom of fruits. Therefore, this method becomes particularly valuable for treatment of fruits wherein the bottoms of the fruit may not be readily exposed, such as for example, fruits in storage rooms and/or chambers. Ultimately, these data demonstrate that the present method using vaporized pyrimethanil may better and less costly to inhibit growth of plant pathogens, such as *P. expansum*, inoculated in fruits (e.g., apples) as compared to more traditional methods of treatment, such as fogging.

Example 13: Distance of Pyrimethanil Application

An in vitro assay was used to evaluate the uniform distribution over distance of the vaporized pyrimethanil treatment as compared to fogging methods of apple treatment. Vaporized treatments of apples were performed as previous described in Examples 1-6, with the exception of using a 1 m wide×1 m high×8 m deep tunnel (see FIG. 11). A 2.66 g amount of pyrimethanil was either fogged or vaporized into the tunnel. The vapor or fog was delivered and distribution was monitored at varying distance (meters) from the source in order to test the effect of treatment distance on distribution.

Figure 24:
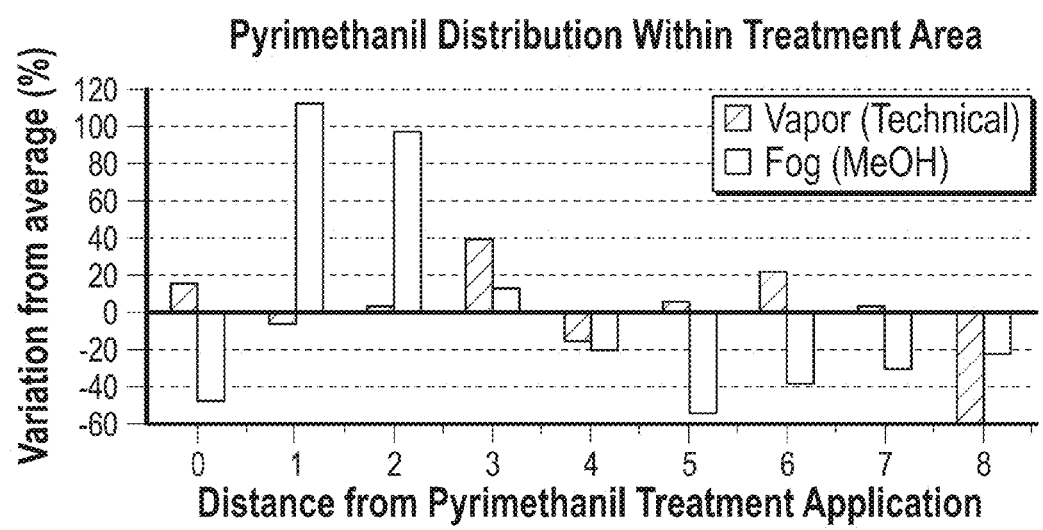
FIG. 24 shows a bar graph comparing the effect of treatment distance on the variation of pyrimethanil distribution on apples treated using a fogging method versus a vaporized method.

Prior to pyrimethanil application, Petri plates of known surface area were placed inside the tunnel and were carefully removed after 72 hours in order to determine the variation of pyrimethanil distribution in the treatment area as a function of pyrimethanil treatment distance from the application source (see FIG. 24). After removal, the pyrimethanil was extracted from the plates and quantified by HPLC.

Results demonstrate that the present method comprising vaporized pyrimethanil provides better in vitro consistency of pyrimethanil distribution as compared to pyrimethanil that was fogged. Vaporized pyrimethanil showed no more than a 40% variation from the average pyrimethanil distribution until the treatment distance was increased to 8 meters, while the fogged pyrimethanil demonstrated almost 50%-110% variation from the average at distances of 1-2 meters and had about a 20%-50% variation at distances of 5-8 meters (see FIG. 24).

The bars shown in FIG. 24 indicate the amount of variation from a 100% uniform application of pyrimethanil compound. Thus, FIG. 24 demonstrates that vaporized pyrimethanil had much more uniform distribution of active ingredient over much higher treatment distances as compared to fogged pyrimethanil.

These data indicate that vaporized pyrimethanil provides a better treatment method of fruit than treatment of fruits by fogging. In particular, the data provided herein demonstrates that the claimed vaporization treatment technique is better to uniformly treat fruit from increased distances of less than 1 meter to about 8 meters, from about 1 meter to about 7 meters, from 1 about meter to about 6 meters, from about 1 meter to about 5 meters, from about 1 meter to about 4 meters, from about 1 meter to about 3 meters, and from about 1 meter to about 2 meters.

Therefore, this method is particularly valuable for uniform treatment of fruits wherein the bottoms of the fruit may not be readily exposed, such as for example, fruits in storage rooms and/or chambers. Ultimately, these data demonstrate that the present method using vaporized pyrimethanil to treat fruit provides better distribution as compared to more traditional methods of fruit treatment, such as fogging.

Example 14: Particle Size of Pyrimethanil Composition

An in vitro assay was performed to estimate the particle sizes of pyrimethanil when delivered by fogging or vaporization. A 2.66 g amount of pyrimethanil was either fogged or vaporized into a treatment tunnel measuring 1 m high×1 m wide×8 m deep (see FIG. 11). Prior to pyrimethanil application, Petri plates of known surface area were placed inside the tunnel and were carefully removed after 7.5, 15, 30, 60, or 360 minutes. After removal, the pyrimethanil was extracted from the plates and quantified by HPLC.

Table 8 results demonstrate that the present method comprising vaporized pyrimethanil provides smaller particle sizes when compared to a fogging application. For example, after 30 minutes, 100% of the fog particles had settled which would correspond to a particle size of approximately 2.8 micron. In comparison, after 30 minutes, there was still no detectable amount of vaporized pyrimethanil settled on the plates. However, after 60 and 360 minutes, 26% and 91% of the total vaporized pyrimethanil had settled, respectively. These settling velocities/rates correspond to an estimated pyrimethanil particle size of 1.9 micron and 0.75 micron, respectively (Table 8).

TABLE 8

Particle Size of Pyrimethanil in Fogging Vs. Vaporization Treatments

| Particle Size (µM) | Settling Time (Minutes) | FOG (MeOH + PYR) | VAPOR (100% Technical PYR) |
|---|---|---|---|
| 5.9 | 7.5 | 61 | — |
| 4.1 | 15 | 77 | — |
| 2.8 | 30 | 100 | — |
| 1.9 | 60 | 100 | 26 |
| 0.75 | 360 | 100 | 91 |

The preceding description enables others skilled in the art to utilize the technology in various embodiments and with various modifications as are suited to the particular use contemplated. In accordance with the provisions of the patent statutes, the principles and modes of operation of this disclosure have been explained and illustrated in exemplary embodiments. Accordingly, the present invention is not limited to the particular embodiments described and/or exemplified herein.

It is intended that the scope of disclosure of the present technology be defined, not only with reference to the above description, but also by the following claims and their equivalents be covered thereby. It should be understood by those skilled in the art that various alternatives to the embodiments described herein may be employed in practicing the claims without departing from the spirit and scope as defined in the following claims. In sum, it should be understood that the disclosure is capable of modification and variation and is limited only by the following claims.

What is claimed is:

1. A method of treating plants or plant parts with an antimicrobial treatment comprising:

a) preparing the antimicrobial treatment comprising an antimicrobial compound, wherein the antimicrobial compound is pyrimethanil or an analog or derivative thereof, b) vaporizing the pyrimethanil or an analog or derivative thereof to form a vapor by sublimation, wherein the sublimation of the pyrimethanil or the analog or derivative thereof occurs via a direct phase transition from the solid phase to the gas phase and skips the intermediate liquid phase, c) cooling the vapor to form solid microparticles, and d) administering the solid microparticles of pyrimethanil or the analog or derivative thereof to one or more plants or plant parts in a chamber.

2. The method of claim 1, wherein the one or more plants or plant parts is selected from the group consisting of a strawberry, a grape, an apple, an orange, and a blueberry.

3. The method of claim 1, wherein the solid microparticles have a size of 2 micron or less.

4. The method of claim 1, wherein the solid pyrimethanil or the analog or derivative thereof is in the form of a powder.

5. The method of claim 1, wherein the pyrimethanil or analog or the derivative thereof comprises the following structure:

6. The method of claim 1, wherein 100% of the pyrimethanil or the analog or derivative thereof is sublimated to produce the vapor.

7. The method of claim 1, wherein no thermal degradation of the pyrimethanil or the analog or derivative thereof occurs at a temperature ranging from about 300° C. to about 350° C.

8. The method of claim 1, wherein the pyrimethanil or the analog or derivative thereof is administered at a rate of about 0.001 mg/L to about 5 mg/L.

9. The method of claim 1, wherein the pyrimethanil or the analog or derivative thereof further comprises a component selected from the group consisting of a carrier, a preservative gas, a compound, and a chemical.

10. The method of claim 9, wherein the preservative gas is $CO_2$ or $SO_2$.

11. The method of claim 1, wherein the method is effective in inhibiting plant pathogens selected from the group consisting of *Acremonium* spp., *Albugo* spp., *Alternaria* spp., *Ascochyta* spp., *Aspergillus* spp., *Botryodiplodia* spp., *Botryospheria* spp., *Botrytis* spp., *Byssochlamys* spp., *Candida* spp., *Cephalosporium* spp., *Ceratocystis* spp., *Cercospora* spp., *Chalara* spp., *Cladosporium* spp., *Colletotrichum* spp., *Cryptosporiopsis* spp., *Cylindrocarpon* spp., *Debaryomyces* spp., *Diaporthe* spp., *Didymella* spp., *Diplodia* spp., *Dothiorella* spp., *Elsinoe* spp., *Fusarium* spp., *Geotrichum* spp., *Gloeosporium* spp., *Glomerella* spp., *Helminthosporium* spp., *Khuskia* spp., *Lasiodiplodia* spp., *Macrophoma* spp., *Macrophomina* spp., *Microdochium* spp., *Monilinia* spp., *Monilochaethes* spp., *Mucor* spp., *Mycocentrospora* spp., *Mycosphaerella* spp., *Nectria* spp., *Neofabraea* spp., *Nigrospora* spp., *Penicillium* spp., *Peronophythora* spp., *Peronospora* spp., *Pestalotiopsis* spp., *Pezicula* spp., *Phacidiopycnis* spp., *Phoma* spp., *Phomopsis* spp., *Phyllosticta* spp., *Phytophthora* spp., *Polyscytalum* spp., *Pseudocercospora* spp., *Pyricularia* spp., *Pythium* spp., *Rhizoctonia* spp., *Rhizopus* spp., *Sclerotium* spp., *Sclerotinia* spp., *Septoria* spp., *Sphaceloma* spp., *Sphaeropsis* spp., *Stemphyllium* spp., *Stilbella* spp., *Thielaviopsis* spp., *Thyronectria* spp., *Trachysphaera* spp., *Uromyces* spp., *Ustilago* spp., *Venturia* spp., *Verticillium* spp., *Bacillus* spp., *Campylobacter* spp., *Clavibacter* spp., *Clostridium* spp., *Erwinia* spp., *Escherichia* spp., *Lactobacillus* spp., *Leuconostoc* spp., *Listeria* spp., *Pantoea* spp., *Pectobacterium* spp., *Pseudomonas* spp., *Ralstonia* spp., *Salmonella* spp., *Shigella* spp., *Staphylococcus* spp., *Vibrio* spp., *Xanthomonas* spp., and *Yersinia* spp.

12. The method of claim 1, wherein the method is effective in inhibiting plant pathogens selected from the group consisting of *Botrytis cinerea, Mucor piriformis, Fusarium sambucinum, Aspergillus brasiliensis*, and *Peniciliium expansum*.

13. The method of claim 1, wherein the chamber is sealed.

14. The method of claim 1, wherein no molecular changes to the pyrimethanil or the analog or derivative thereof is observed during sublimation.

15. The method of claim 1, wherein the method further comprises circulating the solid microparticles of pyrimethanil or the analog or derivative thereof using a source of air flow.

16. The method of claim 15, wherein the source of air flow is one or more fans.

* * * * *